(12) United States Patent
Hatabayashi et al.

(10) Patent No.: US 10,704,073 B2
(45) Date of Patent: Jul. 7, 2020

(54) METHOD FOR DETERMINING UNDIFFERENTIATED STATE OF PLURIPOTENT STEM CELLS BY CULTURE MEDIUM ANALYSIS

(71) Applicant: TOKYO ELECTRON LIMITED, Tokyo (JP)

(72) Inventors: Kunitada Hatabayashi, Tokyo (JP); Kentaro Tomita, Tokyo (JP); Shinichi Gomi, Tokyo (JP); Tomoaki Kurakazu, Stevenage (GB); Yasuhiro Oshima, Stevenage (GB); Kenichi Kagawa, Tokyo (JP); Shigenori Ozaki, Tokyo (JP)

(73) Assignee: TOKYO ELECTRON LIMITED, Tokyo (JP)

( * ) Notice: Subject to any disclaimer, the term of this patent is extended or adjusted under 35 U.S.C. 154(b) by 37 days.

(21) Appl. No.: 15/514,610

(22) PCT Filed: Sep. 29, 2015

(86) PCT No.: PCT/JP2015/077601
§ 371 (c)(1),
(2) Date: Mar. 27, 2017

(87) PCT Pub. No.: WO2016/052558
PCT Pub. Date: Apr. 7, 2016

(65) Prior Publication Data
US 2017/0226558 A1 Aug. 10, 2017

(30) Foreign Application Priority Data
Sep. 29, 2014 (JP) ................................. 2014-199286

(51) Int. Cl.
| | | |
|---|---|---|
| *C12Q 1/02* | (2006.01) | |
| *C12M 1/34* | (2006.01) | |
| *C12M 1/36* | (2006.01) | |
| *C12M 1/00* | (2006.01) | |
| *C12M 1/26* | (2006.01) | |
| *C12N 5/00* | (2006.01) | |
| *G01N 33/50* | (2006.01) | |
| *C12N 5/074* | (2010.01) | |

(52) U.S. Cl.
CPC ............... *C12Q 1/02* (2013.01); *C12M 23/22* (2013.01); *C12M 29/00* (2013.01); *C12M 33/00* (2013.01); *C12M 41/36* (2013.01); *C12M 41/46* (2013.01); *C12M 41/48* (2013.01); *C12N 5/0081* (2013.01); *C12N 5/0696* (2013.01); *G01N 33/5073* (2013.01); *C12N 2500/32* (2013.01); *G01N 2333/47* (2013.01)

(58) Field of Classification Search
None
See application file for complete search history.

(56) References Cited

U.S. PATENT DOCUMENTS

2015/0192568 A1* 7/2015 Shibuya ............ G01N 33/5032
435/14

FOREIGN PATENT DOCUMENTS

| EP | 1816188 A1 | 8/2007 |
|---|---|---|
| EP | 2169048 A2 | 3/2010 |
| JP | 2004215585 A | 8/2004 |
| JP | 2010081805 A | 4/2010 |
| JP | 201445663 A * | 3/2014 |
| JP | 2014045663 A | 3/2014 |
| WO | 2014017480 A1 | 1/2014 |
| WO | 2014208391 A1 | 12/2014 |
| WO | 2013065302 A1 | 5/2015 |
| WO | 2015166845 A1 | 11/2015 |

OTHER PUBLICATIONS

Higuera, G.A. et al. 2012. Patterns of amino acid metabolism by proliferating human mesenchymal stem cells. Tissue Engineering: Part A . 18(5 &6): 654-664.with supplemental data (SD), p. 1-3. specif. pp. 654, 656, SD pp. 1, 3.*
English MT. JP 2014-45663A.Shibuya, K. et al. Method and device for determining degree of stratification and/or differentiation.Date of publication: Mar. 17, 2014.*
Ferrick, D.A. et al. 2008. Advances in measuring cellular bioenergetics using extracellular flux. Drug Discovery Today 13(5/6): 268-274. specif. pp. 268, 269, 270.*
Takahashi, K. et al. 2007. Induction of pluripotent stem cells from adult human fibroblasts by defined factors. Cell 131: 861-872. specif. pp. 861, 862, 867.*
Chen, K.G. et al. Jan. 2014 Human pluripotent stem cell culture: considerations for maintenance, expansion, and therapeutics. Cell Stem Cell 14: 13-26. specif. pp. 13, 14, 15.*
Adewumi, Oluseun et al., "Characterization of Human Embryonic Stem Cell Lines by the International Stem Cell Initiative", Nature Biotechnology vol. 25, No. 7, pp. 803-816, Jun. 17, 2007.
Suzuki, Takashi et al., "Development of Technology for Quality Evaluation of Human Pluripotent Stem Cells by Metabolome Analysis", Shimadzu Review, pp. 123-131, Mar. 31, 2014.
Iwashita, Hidefumi et al., "Secreted Cerebus1 as a Marker for Quantification of Definitive Endoderm Differentiation of the Pluripotent Stem Cells", PloS ONE vol. 8, No. 5, May 2013.
International search report dated Dec. 28, 2015 for international application No. PCT/JP2015/077601.

* cited by examiner

*Primary Examiner* — Thomas J. Visone
*Assistant Examiner* — Sharon M. Papciak
(74) *Attorney, Agent, or Firm* — Nath, Goldberg & Meyer; Jerald L. Meyer

(57) ABSTRACT

There is provided a method for easily determining an undifferentiated state of pluripotent stem cells without relying on the judgment of a skilled technician. The method includes: a step of evaluating an undifferentiated state of pluripotent stem cells based on a time-dependent change in a variation value of an extracellular metabolite contained in a culture medium in which the pluripotent stem cells are cultured, wherein the extracellular metabolite is at least one selected from a group consisting of L-glutamic acid, L-alanine and ammonia.

9 Claims, 21 Drawing Sheets

METHOD FOR DETERMINING UNDIFFERENTIATED STATE OF PLURIPOTENT STEM CELLS BY CULTURE MEDIUM ANALYSIS

This is a National Phase Application filed under 35 U.S.C. 371 as a national stage of PCT/JP2015/077601, filed Sep. 29, 2015, an application claiming the priority benefit of JP 2014-199286 filed Sep. 29, 2014, the content of each of which is hereby incorporated by reference in its entirety.

TECHNICAL FIELD

The present disclosure relates to a method for determining an undifferentiated state of pluripotent stem cells by analyzing a culture medium in which the pluripotent stem cells are cultured.

BACKGROUND

Pluripotent stem cells, due to their differentiation pluripotency capable of being differentiated into any tissue, are widely used in various fields such as a tissue differentiation study, a drug test, a regenerative medicine and the like. In particular, since the establishment of iPS cells, the development of research in this field is remarkable. A variety of efforts for realization of a regenerative medicine has been made all over the word.

However, the pluripotent stem cells are easily differentiated and may possibly lose pluripotency once they are differentiated. Thus, the culture of the pluripotent stem cells needs to be performed while maintaining an undifferentiated state of the pluripotent stem cells. It can be said that the maintenance of the undifferentiated state is one of the most important factors in the culture of the pluripotent stem cells.

In order to maintain the undifferentiated state, the use of a differentiation-inhibiting agent or the removal of differentiation-started pluripotent stem cells is carried out. In the mass production of pluripotent stem cells, one of the problems which may cause the most significant obstacle is the removal of differentiation-started pluripotent stem cells. If the removal of differentiation-started cells is insufficient, there is a possibility that the differentiation of surrounding cells is induced, thereby adversely affecting all the cells under culture. However, it is difficult for an unskilled technician to determine whether pluripotent stem cells are in an undifferentiated state. Under these circumstances, there is naturally a limit in the mass production of pluripotent stem cells. Thus, there is a demand for the development of a method for confirming whether pluripotent stem cells are in an undifferentiated state without relying on at least the judgment of a skilled technician or the development of a method for automatically determining differentiation-started pluripotent stem cells.

Previously, a qRT-PCR method, an immunostaining method or a flow cytometry method has been used as a method for confirming whether pluripotent stem cells are in an undifferentiated state (Non-patent Document 1). However, in the qRT-PCR method and the immunostaining method, it is necessary to destroy cells during measurement. In the flow cytometry method, it is possible to perform non-destructive measurement. However, it is necessary to suspend cells in a single cell state, which requires a complicated operation.

In the meantime. Patent Document 1 discloses a method for non-invasively determining the degree of stratification of cultured cells. However, this method is a method for determining the degree of stratification of cultured cells through the comparison with a predetermined threshold value.

Patent Document 2 discloses a method for determining the degree of stratification and/or differentiation of cultured cells. However, this method is a method for determining the degree of stratification and/or differentiation of cultured cells through the reference to a predetermined correlation database.

Accordingly, a demand still exists for the development of a non-destructive simple method as a method for confirming an undifferentiated state of pluripotent stem cells.

PRIOR ART DOCUMENTS

Patent Documents

Patent Document 1: Japanese laid-open publication No. 2004-215585

Patent Document 2: Japanese laid-open publication No. 2014-045663

Non-Patent Documents

Non-patent Document 1: Nature Biotechnology 25, 803-816 (2007)

The present disclosure provides some embodiments of a method and device for easily determining an undifferentiated state of pluripotent stem cells without relying on the judgment of a skilled technician, and a cell culture apparatus for culturing pluripotent stem cells in an undifferentiated state.

The present inventors have conducted analysis on a metabolite existing in a used culture medium recovered for the replacement with a new culture medium when replacing a medium in a culture process of pluripotent stem cells and have found that it is possible to distinguish undifferentiated pluripotent stem cells and differentiation-started pluripotent stem cells based on a time-dependent change in a variation value of a specific extracellular metabolite (L-glutamic acid. L-alanine and ammonia). The present disclosure is based on this finding.

SUMMARY

That is to say, according to the present disclosure, the following is provided.
(1) A method for determining an undifferentiated state of pluripotent stem cells, including:
a step of evaluating an undifferentiated state of pluripotent stem cells based on a time-dependent change in a variation value of an extracellular metabolite contained in a culture medium in which the pluripotent stem cells are cultured, wherein the extracellular metabolite is at least one selected from a group consisting of L-glutamic acid, L-alanine and ammonia.
(2) The method of (1), wherein the culture medium is a culture medium configured to maintain the undifferentiated state of the pluripotent stem cells.
(3) The method of (1) or (2), wherein the culture medium is obtained as a culture medium used until a subsequent medium replacement after the culture medium is replaced by medium replacement.
(4) The method of (3), wherein a time period of the medium replacement is 24 to 48 hours.
(5) The method of any one of (1) to (4), wherein the variation value is found as a ratio of a variation amount of glutamic acid, L-alanine or ammonia to a variation amount of L-lactic acid which is the extracellular metabolite contained in the culture medium.

(6) The method of any one of (1) to (5), wherein the variation value is a variation value of at least one selected from a group consisting of L-glutamic acid, L-alanine and ammonia, which is available until the subsequent medium replacement after the culture medium is replaced.
(7) The method of any one of (1) to (6), wherein the time-dependent change in the variation value is found as an increasing or decreasing trend of a variation value obtained at each medium replacement time.
(8) The method of any one of (1) to (7), wherein if the variation value shows a decreasing trend as compared with a variation value in a culture medium obtained at an immediately-previous medium replacement time, the pluripotent stem cells are evaluated as being undifferentiated cells.
(9) The method of (8), wherein if the variation value continuously shows the decreasing trend, the pluripotent stem cells are evaluated as being undifferentiated cells.
(10) The method of any one of (1) to (8), wherein if the variation value shows a trend other than a decreasing trend as compared with a variation value in a culture medium obtained at an immediately-previous medium replacement time, the pluripotent stem cells are evaluated as being differentiation-started cells.
(11) The method of any one of (1) to (10), further including:
    a step of evaluating a quality of a colony of the pluripotent stem cells based on a differential-filter-processed image (differential image) of an image of a colony formed by the pluripotent stem cells.
(12) A program for causing a computer to execute the method of any one of (1) to (11).
(13) A computer-readable recording medium which records the program of (12).
(14) A computer which records the program of (12) in an internal storage device.
(15) A system for automatically determining an undifferentiated state of pluripotent stem cells, which includes the computer of (14).
(16) A subculture method of pluripotent stem cells, including:
    a step of recovering cells required in subculture; and
    a step of removing cells not required in culture and/or subculture,
    wherein the cells required in subculture are the pluripotent stem cells evaluated to be undifferentiated cells by the method of any one of (1) to (9) and (11), and the cells not required in culture and/or subculture are the pluripotent stem cells evaluated to be differentiation-started cells by the method of any one of (1) to (7), (10) and (11).
(17) A device for determining an undifferentiated state of pluripotent stem cells, including:
    a recovery means configured to recover a culture medium in which pluripotent stem cells are cultured;
    an analysis means configured to analyze at least one extracellular metabolite selected from a group consisting of L-glutamic acid, L-alanine and ammonia existing in the culture medium recovered by the recovery means; and
    an evaluation means configured to evaluate an undifferentiated state of pluripotent stem cells by finding a time-dependent change in a variation value of the extracellular metabolite based on an analysis result obtained by the analysis means.
(18) A cell culture apparatus for culturing pluripotent stem cells in an undifferentiated state, including:
    an incubation part configured to perform an incubation process with respect to a culture container in which pluripotent stem cells of an undifferentiated state and a medium are accommodated;
    a medium replacement part configured to perform a medium replacement process with respect to the culture container after the incubation process is ended;
    a first medium analysis part configured to perform a first medium analysis process for calculating a variation value of an extracellular metabolite existing in an incubation-processed medium recovered in the medium replacement process;
    an operation control part configured to control operations of the incubation part, the medium replacement part and first medium analysis part so that the incubation process, the medium replacement process and the first medium analysis process are repeated twice or more;
    a cell morphology observation part configured to perform a cell morphology observation process with respect to the culture container at any time after the incubation process is initiated;
    a first determination part configured to perform a first determination process for determining whether the cells existing in the culture container are in an undifferentiated state, based on an observation result obtained in the cell morphology observation process;
    a second medium analysis part configured to perform a second medium analysis process for analyzing a time-dependent change in a variation value of the extracellular metabolite based on the variation value of the extracellular metabolite calculated in the first medium analysis process performed twice or more; and
    a second determination part configured to perform a second determination process for determining whether the cells existing in the culture container are in an undifferentiated state, based on the variation value of the extracellular metabolite and/or the time-dependent change in the variation value of the extracellular metabolite.
(19) The apparatus of (18), wherein the extracellular metabolite is at least one selected from a group consisting of L-glutamic acid, L-alanine and ammonia.
(20) The apparatus of (18) or (19), further including:
    a cell removal part configured to perform a cell removal process for removing differentiation-started cells, based on a determination result obtained in the first determination process and/or a determination result obtained in the second determination process.
(21) The apparatus of any one of (18) to (20), further including:
    an observation condition adjustment part configured to adjust an observation condition in the cell morphology observation process based on a determination result obtained in the second determination process.
(22) A cell culture method for culturing pluripotent stem cells in an undifferentiated state, including:
    (a) a step of performing an incubation with respect to a culture container in which pluripotent stem cells of an undifferentiated state and a medium are accommodated;
    (b) a step of performing a medium replacement with respect to the culture container after the step (a) is ended;
    (c) a step of calculating a variation value of an extracellular metabolite existing in an incubation-processed medium recovered at the step (b);
    (d) a step of repeating the steps (a), (b) and (c) twice or more;
    (e) a step of performing a cell morphology observation with respect to the culture container at any time after the incubation is initiated;
    (f) a step of determining whether the cells existing in the culture container are in an undifferentiated state, based on an observation result obtained at the step (e);

(g) a step of analyzing a time-dependent change in a variation value of the extracellular metabolite based on the variation value of the extracellular metabolite calculated at the step (c) performed twice or more; and (h) a step of determining whether the cells existing in the culture container are in an undifferentiated state, based on the variation value of the extracellular metabolite and/or the time-dependent change in the variation value of the extracellular metabolite.

(23) The method of (22), wherein the extracellular metabolite is at least one selected from a group consisting of L-glutamic acid, L-alanine and ammonia.

(24) The method of (22) or (23), further including:

(i) a step of removing differentiation-started cells based on a determination result obtained at the step (f) and/or a determination result obtained at the step (h).

(25) The method of any one of (22) to (24), further including:

(j) a step of adjusting an observation condition at the step (e) based on a determination result obtained at the step (h).

According to the present disclosure, them is an advantage in that it is not necessary to destroy pluripotent stem cells and it is possible to conduct evaluation based on only an analysis result of a culture medium in which pluripotent stem cells are cultured. Furthermore, according to the analysis of a culture medium, there is no possibility that a value varies greatly as compared with a method of measuring an intracellular metabolite by destroying cells. Information on a time-dependent change of an extracellular metabolite contained in a culture medium can be automatically acquired, recorded and analyzed according to a predetermined program. It is therefore possible to automatically determine an undifferentiated state of pluripotent stem cells. That is to say, there is an additional advantage in that the analysis of a culture medium can be fully automated.

Furthermore, according to the present disclosure, them is an advantage in that the determination of an undifferentiated state of pluripotent stem cells can be performed based on an over-time increasing or decreasing trend of a variation value of a specific extracellular metabolite. That is to say, there is an advantage in that it is not necessary to perform comparison with a predetermined reference value (e.g., a reference value determined by experiments performed in advance, a stored database a metabolic simulation, etc.).

Moreover, according to the present disclosure, it is possible to perform monitoring in a non-destructive manner during a culture process. This makes it possible to inspect all the culture dishes/plates. Thus, there is an advantage in that it is possible to expect uniformity of quality, improvement in yield rate and cost reduction.

In addition, according to the present disclosure, an enzyme electrode method which is an analysis technique that does not require a complicated pretreatment process can be selected as an analysis means of a culture medium. Thus, there is an advantage in that it is possible to build a robust and speedy measurement system.

BRIEF DESCRIPTION OF THE DRAWINGS

FIG. 1A illustrates the cell morphology of the A group.

FIG. 1B illustrates the cell morphology of the B group.
FIG. 1C illustrates the cell morphology of the C group.

FIGS. 4A, 4, 4C and 4D illustrate $\Delta Lac$ vs. $\Delta N$ plot. $\Delta Glu$ vs. $\Delta N$ plot, $\Delta Ala$ vs. $\Delta N$ plot and $\Delta NH_3$ vs. $\Delta N$ plot, respectively.

DETAILED DESCRIPTION

Figure 1A:
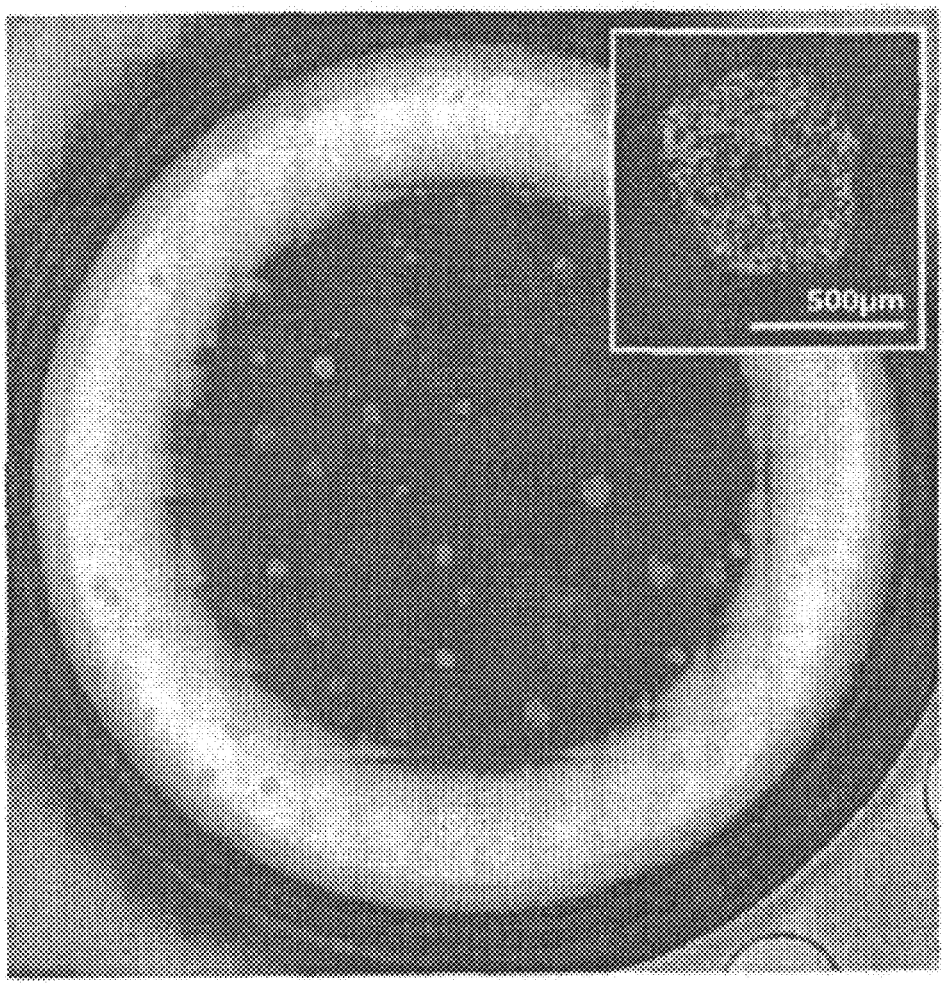
FIGS. 1A, 1B and 1C are views illustrating observation results of (day 7) cell morphologies available 7 days after seeding cells of an A group, a B group and a C group, which are observed by an optical microscope.

In the present disclosure, the expression "determination of an undifferentiated state of pluripotent stem cells" refers to determining whether pluripotent stem cells of interest are in an undifferentiated state.

The expression "pluripotent stem cells" used in the present disclosure refers to cells having an ability to differentiate into cells derived from any of triploblasts. Pluripotent stem cells which form a colony by adhesion culture can be used without any particular limitation. The pluripotent stem cells used in the present disclosure are not particularly limited and may be pluripotent stem cells of mammals such as primate cells, rodent cells or the like, specifically, pluripotent stem cells of a human, a monkey, a mouse, a rat, a guinea pig, a hamster, a rabbit, a cat, a dog, a sheep, a pig, a cow or a goat, more specifically, pluripotent stem cells of a human. The pluripotent stem cells used in the present disclosure may be pluripotent stem cells such as embryonic stem cells (ES cells), induced pluripotent stem cells (iPS cells or artificial pluripolent stem cells). Muse cells (Multilineage-differentiating Stress Enduring Cells), embryonic carcinoma cells (EC cells), embryonic germ stem cells (EG cells) or the like. Preferably, the pluripotent stem cells may be ES cells or iPS cells. Accordingly, the pluripotent stem cells used in the present disclosure may be ES cells or iPS cells of mammals, specifically, ES cells or iPS cells of primates, rodents or the like, more specifically, ES cells or iPS cells of a human, a monkey, a mouse, a rat, a guinea pig, a hamster, a rabbit, a cat, a dog, a sheep, a pig, a cow or a goat, most specifically, ES cells or iPS cells of a human. According to the present disclosure, feeder cells may be used or may not be used.

The expression "culture medium" (also simply referred to as a "medium") refers to a culture medium for maintaining an undifferentiated state of pluripotent stem cells. As the culture medium, a culture medium capable of maintaining an undifferentiated state of pluripotent stem cells can be used without any particular limitation. The culture medium used in the present disclosure is not particularly limited and may be a culture medium obtained by adding a factor, which contributes to maintenance of an undifferentiated state, to a medium capable of culturing pluripotent stem cells. A medium capable of culturing pluripotent stem cells may be used without any particular limitation as long as it can culture pluripotent stem cells. Examples of the medium capable of culturing pluripotent stem cells may include a ReproFF2 medium, an mTeSR1 medium or the like. Examples of the factor which contributes to maintenance of an undifferentiated state may include bFGF, TGF-$\beta$, insulin or the like. The culture medium is replaced by a new culture medium in a predetermined time period during a culture process. Details thereof will be described later.

In the present disclosure, pluripotent stem cells are cultured in a culture container added with the culture medium. As the culture container used in the present disclosure, a culture container capable of culturing pluripotent stem cells can be used without any particular limitation. For example, it may be possible to use a dish, a multi-well plate or the like.

In the present disclosure, during a culture process of pluripotent stem cells, the culture medium may be replaced by a new culture medium in a predetermined time period (medium replacement). The medium replacement time period may be appropriately determined by those skilled in the art and may be, for example, 12 to 72 hours, specifically, 24 to 48 hours.

The expression "during a culture process" refers to a time period during which pluripotent stem cells are seeded and cultured in a culture container added with the culture medium and are then sub-cultured. Pluripotent stem cells may be seeded at such a density that medium replacement is performed 1 to 5 times, specifically, 2 to 4 times, more specifically, 3 to 4 times, during a culture process.

Other culture conditions may be appropriately determined by those skilled in the art depending on the state of pluripotent stem cells used.

According to the present disclosure, by analyzing the culture medium in which pluripotent stem cells are cultured, it is possible to evaluate whether the pluripotent stem cells are in an undifferentiated state.

The culture medium to be used for the analysis may be a culture medium which is replaced by the medium replacement and then used until a subsequent medium replacement. That is to say, the culture medium to be used for the analysis may be recovered from a culture container at the time of medium replacement. For example, when a dish is used as the culture container, the culture medium to be used for the analysis may be recovered as the total amount of the culture medium existing in the dish. For example, when a multi-well plate is used as the culture container, the culture medium to be used for the analysis may be recovered as the total amount of the culture medium existing in each well.

As a culture medium recovery means, a means capable of recovering the culture medium may be used without any particular limitation. For example, the culture medium may be manually recovered using a pipette, a syringe or the like. Alternatively, the culture medium may be recovered using a liquid feeding means provided with a flow path and a pump which are connected to the culture container. From the viewpoint of full automation, it is desirable to use the liquid feeding means.

According to the present disclosure, the evaluation as to whether pluripotent stem cells are in an undifferentiated state may be performed based on a time-dependent change of a variation value of an extracellular metabolite contained in a culture medium.

In the present disclosure, the expression "extracellular metabolite" refers to a metabolite that exists outside a cell (exists in a culture medium) as a result of cell culture. Specifically, the extracellular metabolite is at least one selected from a group consisting of L-glutamic acid, L-alanine and ammonia. That is to say, the amount of extracellular metabolite is an amount obtained by subtracting an amount of a metabolite consumed in a cell from an amount of a metabolite secreted from a cell into a culture medium during the culture of pluripotent stem cells. As can be noted from examples described later, the degree of variation of L-glutamic acid and/or L-alanine and/or ammonia during a culture process may be used as an indicator of evaluation of an undifferentiated state of pluripotent stem cells. L-glutamic acid and/or L-alanine and/or ammonia may be contained in a culture medium as a medium component. However, L-glutamic acid and/or L-alanine and/or ammonia as a p-culture initial medium component does not correspond to an extracellular metabolite.

In the present disclosure, the degree of variation of L-glutamic acid and/or L-alanine and/or ammonia during a culture process is calculated as a "variation value of an extracellular metabolite". Specifically, the "variation value of an extracellular metabolite" may be found as a ratio of a variation amount of L-glutamic acid, L-alanine or ammonia to a variation amount of L-lactic acid which is an extracellular metabolite. As used herein, the expression "variation amount" of each extracellular metabolite contained in a culture medium refers to an amount of an extracellular metabolite contained in a culture medium, which varies as pluripotent stem cells are cultured during a time period from a medium replacement to a subsequent medium replacement. As can be noted from examples described later, the variation amount of L-lactic acid has a strong correlation with the cell proliferation of pluripotent stem cells. Accordingly, it is possible to standardize a variation value based on the variation amount of L-lactic acid.

The reasons why L-lactic acid is suitable for standardization may be as follows.

(1) L-lactic acid is a component not contained in a generally-used culture medium and is an extracellular metabolite which is initially secreted into a culture medium when culturing pluripotent stem cells. For that reason, it is convenient because there is no need to take a difference between a culture medium and a control medium when calculating a variation amount of L-lactic acid.

(2) L-lactic acid is secreted in a large amount as compared with other extracellular metabolites. Thus, it is possible to quantify a variation amount in a more sensitive and accurate manner. This feature works particularly advantageously in the case where the number of seeded cells is small or in the case where the number of culture days is small ($\Delta N$ is small).

As an analysis means of a culture medium, a means capable of measuring an amount of an extracellular metabolite contained in a culture medium may be used without any particular limitation. Examples of the analysis means may include an enzyme electrode method, a colorimetric method, a gas chromatography, a gas chromatography mass spectrometry, a liquid chromatography, a high-speed liquid chromatography mass spectrometry, a capillary electrophoresis mass spectrometry and the like. As an example, it may be possible to use a commercially available analytical instrument such as a BioFlow (trademark) STAT biosensor BM-7M (manufactured by Oji Scientific Instruments Co., Ltd.) which makes use of an enzyme electrode method.

In the present disclosure, as for the variation value of an extracellular metabolite contained in a culture medium, the variation value is measured at every medium replacement time. This makes it possible to find a time-dependent change in the variation value of the extracellular metabolite contained in the culture medium.

In the present disclosure, the expression "time-dependent change of a variation value" refers to a time-dependent change of a variation value obtained at every medium replacement time and may be found as an increasing or decreasing trend of the variation value obtained at every medium replacement time. As used herein, the expression "increasing or decreasing trend" refers to an increase or a decrease in the variation value when compared with a variation value in a culture medium obtained at the just-previous medium replacement time. The increasing or decreasing trend may be determined by comparing the variation value with a variation value in a culture medium obtained at the just-previous medium replacement time.

As can be noted from the examples described later, when the pluripotent stem cells can be kept in an undifferentiated state, the variation value of an extracellular metabolite tends to decrease at every medium replacement time, namely over time. Therefore, according to the present disclosure, the time-dependent change in the variation value may be evaluated as an increasing or decreasing trend of a variation value of an extracellular metabolite contained in a culture medium, which is obtained at every medium replacement time. When evaluating the trend at every medium replacement time, the variation value may be evaluated by comparing the variation value with a variation value in a culture medium, which is obtained at the just-previous medium replacement time.

In the present disclosure, if the variation value shows a decreasing trend as compared with a variation value in a culture medium, which is obtained at the just-previous medium replacement time, the pluripotent stem cells may be evaluated as being undifferentiated cells. In particular, if the decreasing trend is continuously shown (namely, if the decreasing trend is continuously shown twice or more), it can be evaluated that the pluripotent stem cells are undifferentiated cells. On the other hand, if the variation value shows a trend other than the decreasing trend (specifically, an increasing trend or no increase/decrease) as compared with a variation value in a culture medium, which is obtained at the just-previous medium replacement time, it can be evaluated that the pluripotent stem cells are differentiation-started cells. In the time-dependent change, there may be a case where the variation value initially shows an increasing trend and subsequently shows a decreasing trend. In order to achieve determination of high accuracy, even in this case, it can be evaluated, at the time point at which the variation value shows the increasing trend, that the pluripotent stem cells are differentiation-started cells.

As an evaluation means for evaluating an undifferentiated state of pluripotent stem cells, a means capable of finding a time-dependent change of a variation value of an extracellular metabolite based on the analysis result obtained by the analysis means and capable of evaluating an undifferentiated state of pluripotent stem cells may be used without any particular limitation. For example, it is possible to realize automation using a computer or the like.

In the present disclosure, in order to enhance the determination accuracy, it is possible to use, in combination, a method for evaluating a quality of a colony of pluripotent stem cells based on a differential-filter-processed image (differential image) of an image of a colony formed by pluripotent stem cells. The method may be implemented according to the descriptions of Japanese laid-open publication No. 2014-18184. Specifically, the method is as follows.

(1) A method for evaluating a quality of a colony of pluripotent stem cells based on a differential-filter-processed image (differential image) of an image of a colony formed by pluripotent stem cells.

(2) The method according to (1), wherein the quality of the colony is evaluated based on an image pattern obtained from the differential image of the pluripotent stem cells.

(3) The method according to (1), wherein digitization is performed from the differential image for each pixel according to the tone of each pixel and then the quality of the colony is evaluated based on a numerical value of a central portion of the colony, in some cases, based on a numerical value of a peripheral portion of the colony.

(4) The method according to (1), wherein digitization is performed from the differential image for each pixel according to the tone of each pixel and then the quality of the colony is evaluated based on a numerical value distribution thus obtained.

(5) The method according to (4), wherein digitization is performed from the differential image for each pixel according to the tone of each pixel and then the quality of the colony is evaluated by curve-fitting at least one kind of fit function created in advance for the numerical value distribution of the colony to the numerical value distribution of the colony to be evaluated.

(6) The method according to (5), wherein the fit function created in advance is at least one kind of fit function including a fit function ($f_{good}$ function) which indicates a convex shape and/or a fit function ($f_{bad}$ function) which indicates a convex shape in the central portion of the colony and indicates a convex shape in the peripheral portion of the colony (where a graph of a fit function is crated by indicating a position of a straight line passing through the central portion of the colony on a horizontal axis (X axis) of a plane rectangular coordinate system and indicating a numerical value distribution on a vertical axis (Y axis)).

(7) The method according to (6), wherein the fit function created in advance is at least two kinds of fit functions including the $f_{good}$ function and the $f_{bad}$ function.

(8) The method according to (6) or (7), wherein the $f_{bad}$ function meets one, two or all conditions selected from: (condition B1) that the $f_{bad}$ function converges in the limit of x→−∞ and x→∞; (condition B2) that the $f_{bad}$ function is zero or more with respect to an arbitrary real number x within the colony; and (condition B3) that the $f_{bad}$ function has one minimum value and two maximum values within the colony.

(9) The method according to any one of (6) to (8), wherein the $f_{bad}$ function is selected from a group consisting of:

$$f_{bad}(x) = A_0 + A_1\exp\left\{\frac{-(x-x_1)^2}{2w_1^2}\right\} + A_2\exp\left\{\frac{-(x-x_2)^2}{2w_2^2}\right\};$$ [Mathematical formula 1]

$$f_{bad}(x) = A_0 + A_1\left[\frac{w}{\{4(x-x_1)^2 + w_1^2\}}\right] + A_2\left[\frac{w}{\{4(x-x_2)^2 + w_2^2\}}\right];$$ [Mathematical formula 2]

$$f_{bad}(x) = A_0 + A_1\exp[1 + a_1(x-x_1) - \exp\{b_1(x-x_1)\}] + A_2\exp\left[\frac{1 + a_2(x-x_2) -}{\exp\{b_2(x-x_2)\}}\right]; \text{ and}$$ [Mathematical formula 3]

$$f_{bad}(x) = A_0 + A_1(x-x_0) + A_2(x-x_0)^2 + A_3(x-x_0)^3 + A_4(x-x_0)^4.$$ [Mathematical formula 4]

(10) The method according to (9), wherein the $f_b$ function is $$f_{bad}(x) = A_0 + A_1(x-x_0) + A_2(x-x_0)^2 + A_3(x-x_0)^3 + A_4(x-x_0)^4$$ [Mathematical formula 5]

(11) The method according to any one of (6) to (10), wherein the $f_{good}$ function meets one, two or all conditions selected from: (condition G1) that the $f_{good}$ function converges in the limit of x→−∞ and x→∞; (condition G2) that the $f_{good}$ function is zero or more with respect to an arbitrary real number x within the colony; and (condition G3) that the $f_{good}$ function has one maximum value within the colony.

(12) The method according to any one of (6) to (11), wherein the $f_{good}$ function is selected from a group consisting of:

$$f_{good}(x) = A_0 + A_1\exp\left\{-\frac{(x-b)^2}{2c^2}\right\};$$ [Mathematical formula 6]

$$f_{good}(x) = A_0 + A_1\left[\frac{w}{\{4(x-x_1)^2 + w_1^2\}}\right]; \text{ and}$$ [Mathematical formula 7]

$$f_{good}(x) = A_0 + A_1\{0.5 + 1/\pi\arctan[a_1((x-x_0) + x_1)]\} \{0.5 + 1/\pi\arctan[a_2((x-x_0) - x_1)]\}.$$ [Mathematical formula 8]

(13) The method according to (12), wherein the $f_{good}$ function is $$f_{good}(x) = A_0 + A_1\{0.5 + 1/\pi\arctan[a_1((x-x_0) + x_1))]\} \{0.5 + 1/\pi\arctan(a_2((x-x_0) - x_1))\}$$ [Mathematical formula 9]

(14) The method according to any one of (6) to (13), wherein the quality of the colony is evaluated by using, as an indicator, the degree of deviation between at least one kind of approximate curve obtained by curve fitting and a numerical value distribution of the colony to be evaluated.

(15) The method according to any one of (6) to (13), wherein the quality of the colony is evaluated by using, as an indicator, a parameter extracted from at least one kind of approximate curve obtained by curve fitting.

(16) The method according to (15), wherein the parameter is one or more parameters selected from a group consisting of a maximum value of the $f_{good}$ function, a maximum value of the $f_{bad}$ function, a minimum value of the $f_{bad}$ function, a maximum value of a actually-measured value and a minimum value of the actually-measured value, within the colony.

(17) The method according to (15) or (16), wherein the quality of the colony is evaluated by using, as an indicator, the sum, difference, product or ratio of two parameters.

(18) The method according to (17), wherein the quality of the colony is evaluated by using, as an indicator, the sum, difference, product or ratio between a value of the sum, difference, product or ratio of two parameters and a value of the sum, difference, product or ratio of another two parameters in a combination of the another two parameters.

(19) The method according to (17) or (18), wherein the parameters are two parameters selected from a group consisting of a maximum value of the $f_{good}$ function, a maximum value of the $f_{bad}$ function and a minimum value of the $f_{bad}$ function within the colony.

(20) The method according to (18), wherein the quality of the colony is evaluated based on at least one parameter selected from a group consisting of the following four parameters calculated from an approximate curve for each colony:

Parameter A which is a difference between a value of a central portion of the $f_{good}$ function and a minimum value of the $f_{bad}$ function;

Parameter B which is a difference between a maximum value and a minimum value of the $f_{bad}$ function;

Parameter C which is a difference between a maximum value of the actually-measured value and a minimum value of the actually-measured value in the central portion of the colony; and Parameter D which is a mean square of a difference between the $f_{good}$ function and the actually-measured value within the colony.

(21) The method according to (20), wherein the quality of the colony is evaluated based on a numerical value obtained by weighing and adding two or more parameters selected from parameters A to D.

In the present disclosure, in order to enhance the determination accuracy, cell morphology observation may be used in combination.

According to the present disclosure, the whole process of evaluating the undifferentiated state of the pluripotent stem cells based on the analysis result of the culture medium in which the pluripotent stem cells are cultured may be automated by a computer or the like. Thus, there is provided a program for causing a computer to execute the method of the present disclosure. Specifically, according to the present disclosure, there is provided a program for causing a computer to execute a step of obtaining an analysis result of a culture medium in which pluripotent stem cells are cultured and a step of automatically determining an undifferentiated state of pluripotent stem cells based on the analysis result. Furthermore, according to the present disclosure, there is provided a computer-readable recording medium which records the program of the present disclosure. Moreover, according to the present disclosure, there is provided an automatic determination system for evaluating an undifferentiated state of pluripotent stem cells, which includes a computer for recording the program of the present disclosure in an internal recording device thereof or a computer of the present disclosure.

The program of the present disclosure may be recorded in a recording medium such as a flexible disk, a CD-ROM or the like and may be executed by causing a computer to read the same. The recoding medium is not limited to a removable recording medium such as a magnetic disk, an optical disk or the like but may be a fixed recording medium such as a hard disk device, a memory or the like. Furthermore, the program of the present disclosure may be distributed via a communication line such as the Internet or the like (including wireless communication). Moreover, the program of the present disclosure may be encrypted, modulated or compressed and may be distributed via a wired line or a wireless line such as the Internet or the like or by recording the same in a recording medium.

According to the determination method of the present disclosure, it is possible to evaluate an undifferentiated state of pluripotent stem cells without destroying the pluripotent stem cells. If it is evaluated by this method that the pluripotent stem cells are undifferentiated cells, the culture is continuously performed. On the other hand, if it is evaluated by this method that the pluripotent stem cells are differentiation-started cells, the pluripotent stem cells may be removed. Accordingly, the determination method according to the present disclosure is applicable to a subculture method of pluripotent stem cells.

In the subculture method of the present disclosure, the cells evaluated as being differentiation-started cells by the determination method of the present disclosure are regarded as cells unnecessary in the culture and/or the subculture and may be removed. In this regard, the removal of the unnecessary cells may be performed during the culture or may be performed at the time of subculture. In view of the feature of the present disclosure in which the analysis of the culture medium is performed, the removal of the unnecessary cells may be performed for each culture container (for each well in the case of using a multi-well plate as the culture container).

One aspect of the subculture method of the present disclosure includes:

(i) a step of seeding pluripotent stem cells in a culture container added with a culture medium;

(ii) a step of culturing the pluripotent stem cells seeded at step (i);

(iii) a step of analyzing the culture medium recovered at each medium replacement time during the culture of step (ii);

(iv) a step of evaluating an undifferentiated state of the pluripotent stem cells by finding a time-dependent change in a variation value of at least one extracellular metabolite selected from a group consisting of L-glutamic acid, L-alanine and ammonia, based on an analysis result obtained at step (iii);

(v-1) a step of separating the pluripotent stem cells evaluated as being in an undifferentiated state at step (iv) from the culture container and seeding the pluripotent stem cells in another culture container; and (v-2) a step of removing the pluripotent stem cells evaluated at step (iv) to have started differentiation, wherein steps (i) to (v) are appropriately repeated.

In this aspect, a method of evaluating the quality of a colony of the pluripotent stem cells based on a differential-filter-processed image (differential image) of an image of a colony formed by the pluripotent stem cells may be used in combination. In the case where the method is used in combination, the quality of the colony of the pluripotent stem cells may be evaluated independently of the evaluation performed at step (iv) and the colony may be selected, separated and removed.

In this aspect, a cell morphology observation may be used in combination. In the case where the cell morphology observation is used in combination, the cell morphology of the pluripotent stem cells may be observed independently of the evaluation performed at step (iv) and the cells may be selected, separated and removed.

According to the present disclosure, there is provided a device for determining an undifferentiated state of pluripotent stem cells, including:

a recovery means configured to recover a culture medium in which the pluripotent stem cells are cultured;

an analysis means configured to analyze at least one extracellular metabolite selected from a group consisting of L-glutamic acid, L-alanine and ammonia existing in the culture medium recovered by the recovery means; and an evaluation means configured to evaluate the undifferentiated state of the pluripotent stem cells based on a time-dependent change in a variation value of the extracellular metabolite, which is obtained by the analysis means.

The recovery means, the analysis means and the evaluation means of the device according to the present disclosure are as described above.

Figure 8A:
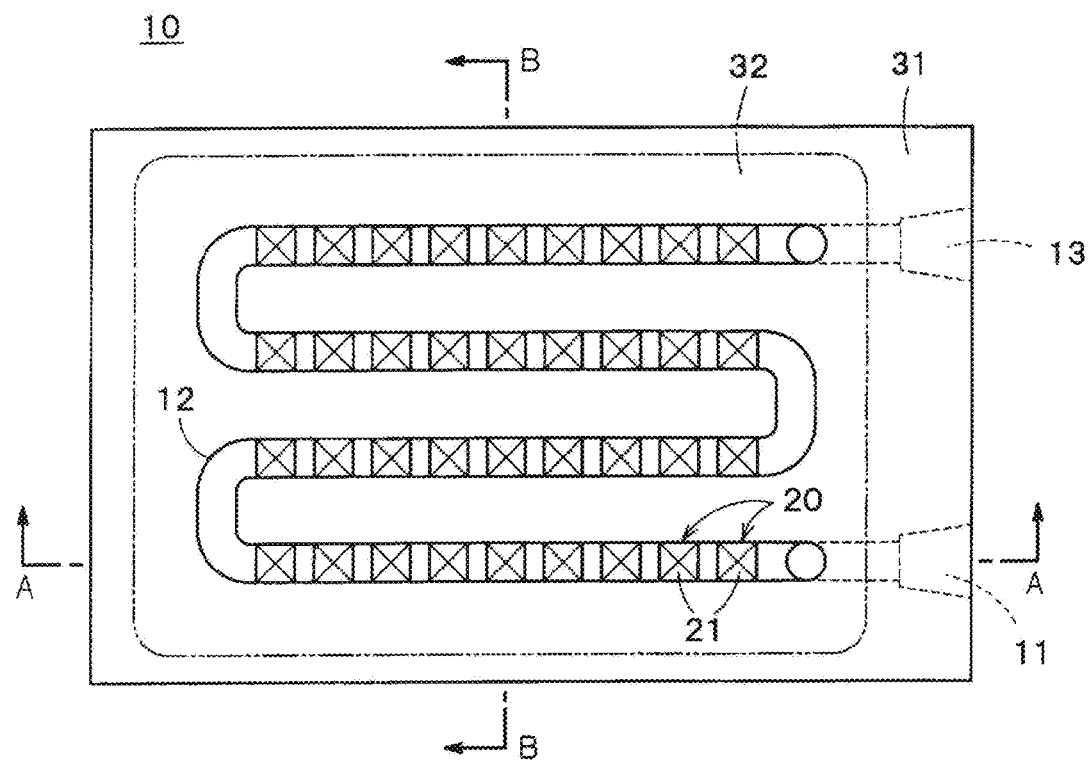
FIG. 8A is a schematic plan view of a culture container used in a cell culture apparatus according to one embodiment of the present disclosure.
Figure 8B:
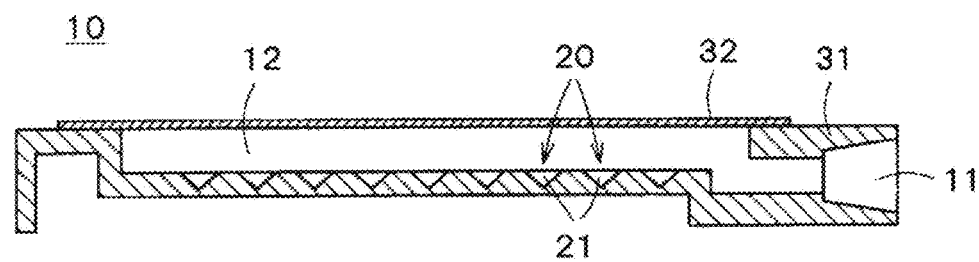
FIG. 8B is a sectional view taken along line A-A in FIG. 8A.
Figure 8C:
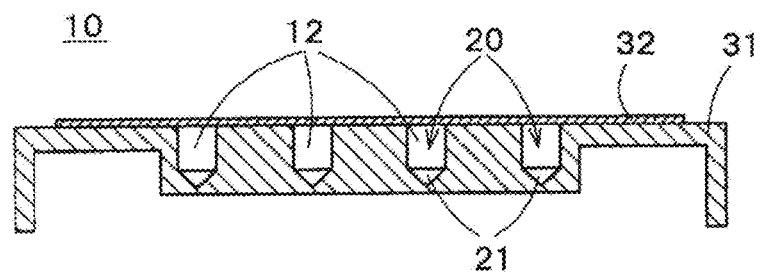
FIG. 8C is a sectional view taken along line B-B in FIG. 8A.

Hereinafter, a cell culture apparatus according to one embodiment of the present disclosure will be described with reference to the drawings. First, a culture container used in the cell culture apparatus according to one embodiment of the present disclosure will be described with reference to FIGS. 8A to 8C. FIG. 8A is a schematic plan view of the culture container used in the cell culture apparatus according to one embodiment of the present disclosure. FIG. 8B is a sectional view taken along line A-A in FIG. 8A. FIG. 8C is a sectional view taken along line B-B in FIG. 8A.

As illustrated in FIGS. 8A to 8C, the culture container used in the present embodiment is a culture container 10 of a closed system. As illustrated in FIGS. 8A to 8C, the culture container 10 includes a container body 31 having a concave flow path 12, and a flat plate 32 configured to seal an opening of the flow path 12. As the material of the container body 31 and the flat plate 32, it may be possible to use, for example, a synthetic resin (e.g., polystyrene) having a light transmitting property. If the container body 31 and the flat plate 32 have a light transmitting property, it is possible to optically observe the cells existing in the culture container 10 from the outside.

As illustrated in FIG. 8A, the container body 31 includes an inlet port 11 through which a liquid is introduced, a flow path 12 through which the liquid introduced from the inlet port 11 passes, and an outlet port 13 through which the liquid fluid passed through the flow path 12 is discharged. The inlet port 11, the flow path 12 and the outlet port 13 are integrally formed by, for example, an injection molding.

As illustrated in FIGS. 8 and 8C, the flow path 12 of the container body 31 is formed as a recess portion (groove portion) opened toward one side of the container body 31. Furthermore, as illustrated in FIG. 8A, the flow path 12 of the container body 31 has a winding shape in a plan view.

As illustrated in FIG. 8A, on a bottom surface of the flow path 12, a plurality of cell seeding regions 20, in which cells are seeded, is installed side by side along the flow path 12. It is preferred that the surface roughness of a region other than the cell seeding regions 20 in the bottom surface of the flow path 12 is larger than the surface roughness of the cell seeding regions 20. For example, the surface roughness of the cell seeding regions 20 may be Ra 0.2 or less and the surface roughness of the region other than the cell seeding regions 20 may be Ra 0.8 or less. The term "Ra" used herein refers to an arithmetic average roughness and is in compliance with the provision of JIS B0601. Such a difference in the surface roughness may be realized by adjusting the surface roughness of a mold used when injection-molding the container body 31. As the surface roughness of the region other than the cell seeding regions 20 grows larger, it becomes more difficult for the cells to adhere to the region other than the cell seeding regions 20.

As illustrated in FIGS. 8B and 8C, on the bottom surface of the flow path 12, depressions 21 are formed in a concentric relationship with the cell seeding regions 20. In the illustrated example, the shape of the depressions 21 is a square pyramidal shape. However, the shape of the depressions 21 is not particularly limited but may be a pyramidal shape, a conical shape, a cylindrical shape, a prismatic shape or a dome shape other than the square pyramidal shape.

It is preferred that the apex angle of the depressions 21 is 30 to 90 degrees. If the apex angle of the depressions 21 is larger than 90 degrees, it becomes difficult for the cells to slide down along the slam surfaces of the depressions 21. Furthermore, if the apex angle of the depressions 21 is smaller than 30 degree, it becomes difficult for the cells to fall down from the inner side of the depressions 21 when the culture container is upside down.

The inlet port 11 and the outlet port 13 of the container body 31 are formed on the same lateral surface of the container body 31. However, the inlet port 11 and the outlet port 13 may be formed on different lateral surfaces. The inlet port 11 communicates with one end of the flow path 12. The outlet port 13 communicates with the other end of the flow path 12. While not shown in the drawings, in the inlet port 11 and the outlet port 13, there may be installed a robber plug with a slit into which a tip of a syringe can be inserted, an elastic membrane into which a needle can be stabbed, or a structure including an opening/closing valve used in medical applications such as a Luer lock or the like. This makes it possible to reduce a risk of contamination from the outside at the time of injection and recovery of a liquid.

The flat plate 32 is formed thin so as to have moderate gas permeability. The thickness of the flat plate 32 may be, for example, 50 to 200 μm. This makes it easy to supply a gas such as an oxygen gas or the like to the cells under culture. In the case of culturing anaerobic cells, it is preferred that the flat plate 32 has gas impermeability. In this case, the thickness of the flat plate 32 may be, for example, 2000 to 3000 μm.

In order to seal the opening of the flow path 12, the flat plate 32 is disposed on the entire surface of the container body 31 on which the opening of the flow path 12 is formed. The flat plate 32 is affixed to and fixedly supported by the wall portion of the container body 31 (the edge region of the wall portion that defines the flow path 12). In the present embodiment, the flat plate 32 is bonded to the container body 31 by an adhesive agent. However, the fixing method is not limited to the adhesive bonding but may be, for example, a thermal welding, an ultrasonic welding or the like.

The culture container 10 may be manufactured in the following manner. First, the surface of the container body 31 having the flow path 12, to which the flat plate 32 is not yet affixed, is subjected to an $O_2$ plasma process. For example, an $O_2$ gas is converted to plasma by electric power having an appropriate wattage. The $O_2$ plasma is applied to the surface of the container body 31 having the flow path 12 for a predetermined time. Then, the flow path 12 of the container body 31 is processed with a cell-non-adhesive coating solution. For example, a cell-non-adhesive coating solution is caused to flow into the flow path 12 and is allowed to stay at 37 degrees C. for a predetermined time. Thereafter, the cell-non-adhesive coating solution is caused to flow out from the flow path 12. The flow path 12 is washed with sterile water. Then, the flat plate 32 is affixed to one surface of the container body 31 in which the flow path 12 is formed.

For example, an adhesive agent is coated on the edge region of the wall portion of the container body 31. Thereafter, the flat plate 32 is placed on the container body 31 so as to cover the opening of the flow path 12 and is bonded by the adhesive agent. Then, the adhesive agent is dried and solidified.

It is preferred that the following pretreatment is performed before the culture container 10 is used in cell culture. First, a PBS solution is caused to flow into the flow path 12 from the inlet port 11, thereby filling the flow path 12 with the PBS solution. Thus, air bubbles are removed from the flow path 12. Then, an extracellular matrix (ECM) is caused to adhere to a portion of the flat plate 32 facing the depressions 21. For example, an ECM solution is caused to flow into the flow path 12 from the inlet port 11. The PBS solution existing in the flow path 12 is pushed by the ECM solution and is discharged from the outlet port 13. The state in which the flow path 12 is filled with the ECM solution is maintained for a predetermined time. Thus, the ECM adheres to a region of the flow path 12 on which the cell-non-adhesive coating solution is not coated, namely the entire region of the flat plate 32 which corresponds to the opening of the flow path 12. The ECM serves as a scaffold for the cells during the cell culture.

Figure 9:
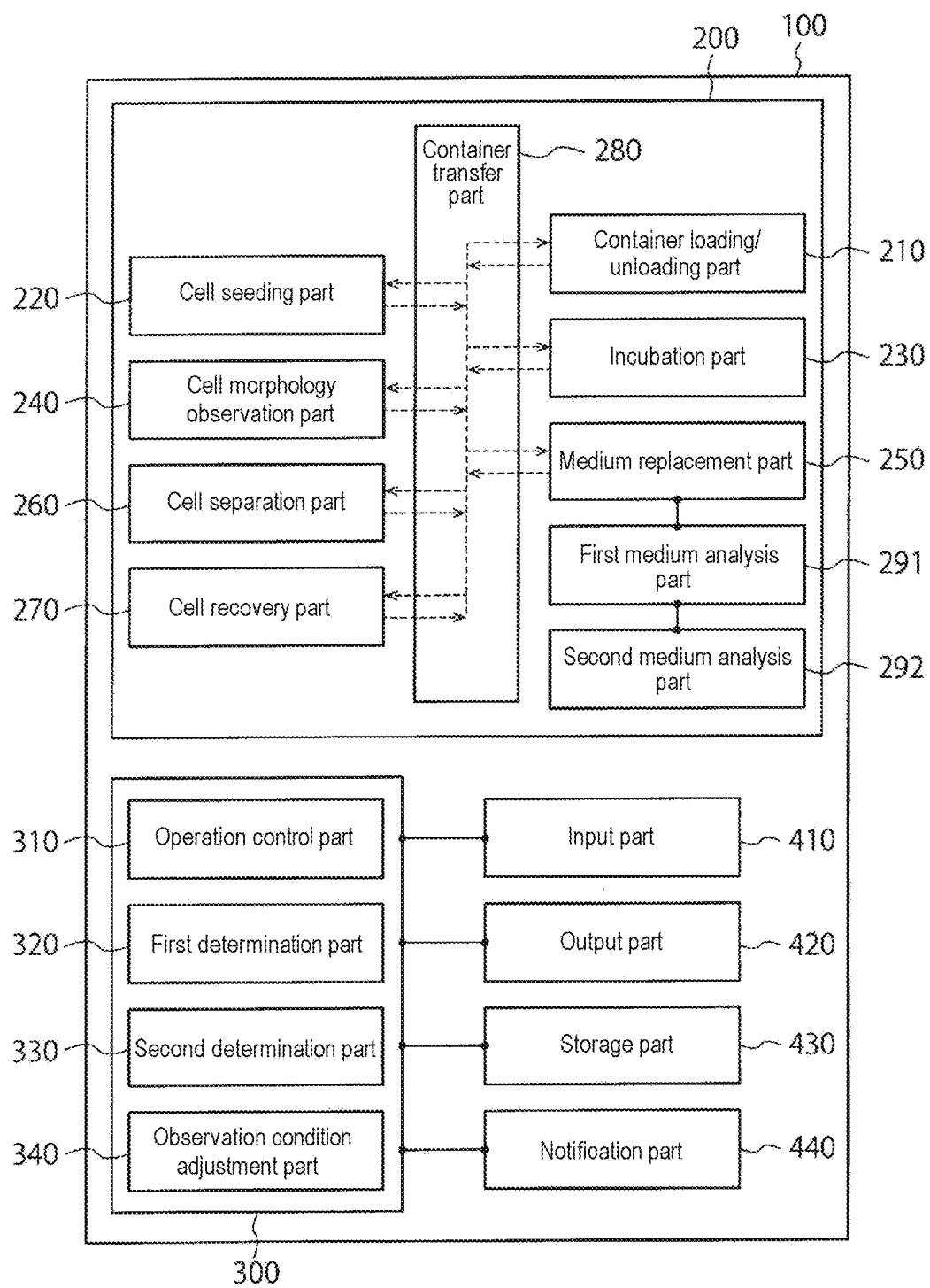
FIG. 9 is a schematic diagram illustrating the configuration of a cell culture apparatus according to one embodiment of the present disclosure.

Next, the cell culture apparatus according to one embodiment of the present disclosure will be described with reference to FIG. 9. FIG. 9 is a schematic view illustrating the configuration of the cell culture apparatus according to one embodiment of the present disclosure. In FIG. 9, the connection of wiring lines is indicated by solid lines and a container transfer route is indicated by broken lines.

The cell culture apparatus 100 according to the present embodiment is a cell culture apparatus for culturing pluripotent stem cells in an undifferentiated state. The cell culture apparatus 100 can culture pluripotent stem cells in an undifferentiated state by culturing the pluripotent stem cells while determining whether the pluripotent stem cells are in an undifferentiated state (in some cases, while removing the differentiation-started cells identified by the respective determination) through the combined use of a cell state determination based on a cell morphology observation and a cell state determination based on analysis of components of a medium used in cell culture.

As illustrated in FIG. 9, the cell culture apparatus 100 includes a cell processing part 200, a control part 300, an input part 410, an output part 420, a storage part 430 and a notification part 440.

The cell processing par 200 is an operation part configured to perform various kinds of processes with respect to a container, cells contained in the container or a medium. The cell processing part 200 includes a container loading/unloading part 210, a cell seeding part 220, an incubation part 230, a cell morphology observation part 240, a medium replacement part 250, a cell separation part 260, a cell recovery part 270 and a container transfer part 280. The cell processing part 200 further includes a first medium analysis part 291 and a second medium analysis part 292, both of which performs a medium analysis process.

The cell processing part 200 performs a series of processes for culturing cells in a desired state, including a cell loading/unloading process performed by the container loading/unloading part 210, a cell seeding process performed by the cell seeding pant 220, an incubation process performed by the incubation part 230, a cell morphology observation process performed by the cell morphology observation part 240, a medium replacement process performed by the medium replacement part 250, a cell separation process performed by the cell separation part 260, a cell recovery process performed by the cell recovery part 270 and a medium analysis process performed by the first medium analysis part 291 and the second medium analysis part 292.

The container loading/unloading part 210 perform a cell loading process and a cell unloading process. In the cell loading process, the container loading/unloading part 210 loads a container, which contains cells to be seeded in the culture container 10, from outside of the cell culture apparatus 100. In the cell unloading process, the container loading/unloading past 210 unloads the culture container 10, the process of which is completed in the cell processing part 200 or the culture container 10, the process of which is stopped in the cell processing part 200, to outside of the cell culture apparatus 100.

The cell seeding part 220 performs a cell seeding process with respect to the culture container 10. In the cell seeding process, the cell seeding part 220 seeds cells in a new culture container 10 not used in the cell culture. At this time, cells and a medium are accommodated in the culture container 10. The cells seeded in the culture container 10 are pluripotent stem cells of an undifferentiated state.

Figure 10:
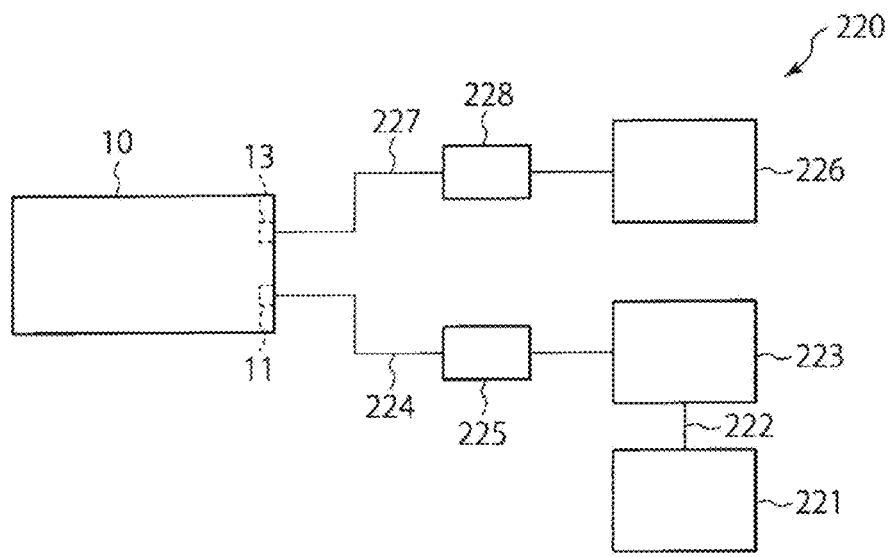
FIG. 10 is a schematic plan view illustrating the configuration of a cell seeding pan.

A configuration example of the cell seeding part 220 is illustrated in FIG. 10. As illustrated in FIG. 10, the cell seeding part 220 includes a cell suspension preparation part 221, a cell supply tank 223 configured to store a cell suspension supplied from the cell suspension preparation part 221 via a supply flow path 222, an inflow conduit 224 connectable at one end to the inlet port 11 of the culture container 10 and connected at the other end to the cell supply tank 223, a flow rate regulator 225 such as a valve, a pump or the like installed in the inflow conduit 224, a cell recovery tank 226, an outflow conduit 227 connectable at one end to the outlet port 13 of the culture container 10 and connected at the other end to the cell recovery tank 226, and a flow rate regulator 228 such as a valve, a pump or the like installed in the outflow conduit 227.

The cell suspension preparation part 221 collects cells from a container, which accommodates cells (pluripotent stem cells of an undifferentiated state) to be seeded in the culture container 10, through the use of a cell picker or the like, prepares a cell suspension from the cells thus collected, and supplies the prepared cell suspension from the supply flow path 222 to the cell supply tank 223.

The cell seeding part 220 supplies the cell suspension stored in the cell supply tank 223 to the culture container 10 via the inflow conduit 224 connected to the inlet port 11 of the culture container 10. Furthermore, the cell seeding part 220 causes the cell recovery tank 226 to recover the cell suspension flowing out from the outlet port 13 of the culture container 10 through the outflow conduit 227 connected to the outlet port 13 of the culture container 10.

When the cell suspension supplied to the culture container 10 passes through the flow path 12, the cells existing in the cell suspension fall (precipitate) onto the bottom surface of the flow path 12. In the present embodiment, the surface roughness of the region other than the cell seeding regions 20 in the bottom surface of the flow path 12 is relatively large. Thus, it becomes difficult for the cells to adhere to the region other than the cell seeding regions 20.

After the cells fall (precipitate) onto the bottom surface of the flow path 12, the cell seeding part 220 causes a vibration mechanism (not shown) to vibrate the culture container 10 substantially in the horizontal direction. Thus, the cells falling onto the region other than the depressions 21 in the bottom surface of the flow path 12 are guided into the depressions 21, whereby the cells aggregate inside the cell seeding regions 20. Then, the cell seeding part 220 causes an inversion mechanism (not shown) to invert the culture container 10 upside down. Thus, the cells aggregated inside the depressions 21 fall onto a portion facing the depressions 21 in the flat plate 32. The ECM is coated on the portion facing the depressions 21 in the flat plate 32. Thus, the cells falling onto the flat plate 32 are cultivated and proliferated using the ECM as a scaffold, thereby forming a colony.

The incubation part 230 performs an incubation process with respect to the culture container 10 which accommodates the pluripotent stem cells of an undifferentiated state and the medium. In the incubation process, the incubation part 230 places the culture container 10 under an environment suitable for cell culture, thereby cultivating and proliferating the cells contained in the culture container 10.

The incubation process performed by the incubation part 230 is performed on a medium-by-medium basis. Accordingly, an incubation process for the culture container 10 accommodating a certain medium and an incubation process for the culture container 10 accommodating a newly replaced medium are different incubation processes. The incubation process for the culture container 10 accommodating a certain medium is performed from the start of the incubation process to the end of the incubation process. The incubation process may be performed continuously or may be performed intermittently. For example, during the time period from the start of the incubation process to the end of the incubation process, the culture container 10 accommodating a certain medium may be held within the incubation part 230 and the incubation process for the culture container 10 may be performed continuously. Furthermore, after the start of the incubation process, the incubation process may be interrupted in order to perform a process (e.g., a cell morphology observation process or a cell separation process) other than the incubation process with respect to the culture container 10. At the end of the process, the incubation process may be resumed without performing a medium replacement process. The expression "the start of the incubation process" includes not only a case where the incubation process is started with respect to the culture container 10 accommodating a fresh medium not subjected to the incubation process but also a case where, after starting the incubation process with respect to the culture container 10 accommodating a fresh medium not subjected to the incubation process, the incubation process is interrupted in order to perform a process (e.g., a cell morphology observation process or a cell separation process) other than the incubation process with respect to the culture container 10 and, after terminating the process, the incubation process is resumed without performing a medium replacement process. The expression "the end of the incubation process" means that the incubation process for the culture container 10 accommodating a certain medium is no longer performed. In the case where, after starting the incubation process, the incubation process is interrupted in order to perform a process (e.g., a cell morphology observation process or a cell separation process) other than the incubation process with respect to the culture container 10 and, after terminating the process, the incubation process is resumed without performing a medium replacement process, the interruption of the incubation process does not correspond to the end of the incubation process. The incubation process is terminated, for example, if the incubation process is performed for a predetermined time (e.g., 24 hours) with respect to the culture container 10 accommodating a certain medium (namely, if the incubation process is performed for a predetermined time with respect to the same medium).

Figure 11:
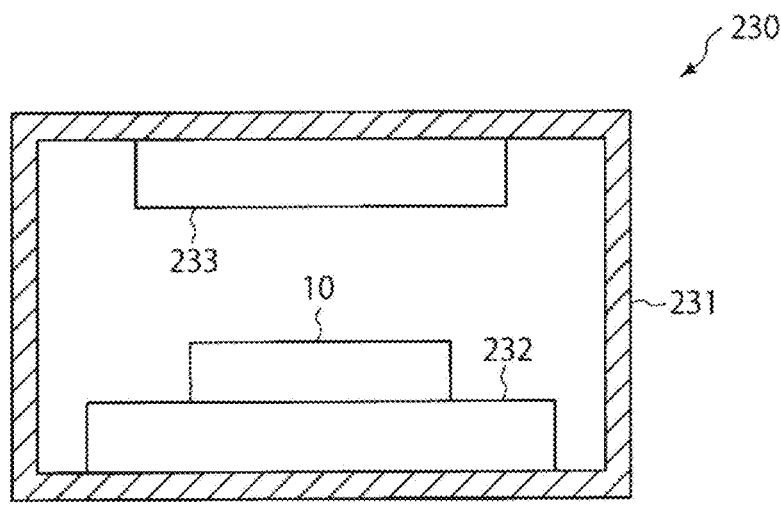
FIG. 11 is a schematic sectional view illustrating the configuration of an incubation part.

A configuration example of the incubation part 230 is illustrated in FIG. 11. As illustrated in FIG. 11, the incubation part 230 includes a container accommodation part 231 capable of accommodating one or more culture containers 10, a mounting pan 232 on which one or more culture containers 10 are mounted, and an environment adjustment part 233 configured to maintain an internal atmosphere of the container accommodation part 231 in an environment suitable for cell culture. The environment adjustment part 233 may adjust the internal atmosphere of the container accommodation part 231 to have a condition suitable for cell culture (e.g., a temperature of 37 degrees C., a humidity of 90% and a $CO_2$ concentration of 5%).

The cell morphology observation part 240 performs a cell morphology observation process with respect to the culture container 10. In the cell morphology observation process the cell morphology observation part 240 observes the morphology of the cells existing in the culture container 10 and acquires an observation image as an observation result. The cell morphology observation is performed, for example, on a colony-by-colony basis.

The culture container 10 subjected to the cell morphology observation is the culture container 10 available at any time after the start of the incubation process. The expression "any time after the start of the incubation process" includes any time after the interruption of the incubation process and any time after the end of the incubation process. In the case where the incubation process and the medium replacement process performed after the end of the incubation process are repeatedly performed twice or more, the culture container 10 subjected to the cell morphology observation may be the culture container 10 accommodating an incubation-processed medium (namely, the culture container 10 available after the start of the incubation process but before the medium replacement process) or may be the culture container 10 accommodating a fresh medium not subjected to the incubation process (namely, the culture container 10 available after the medium replacement process but before the start of the incubation process).

Figure 12:
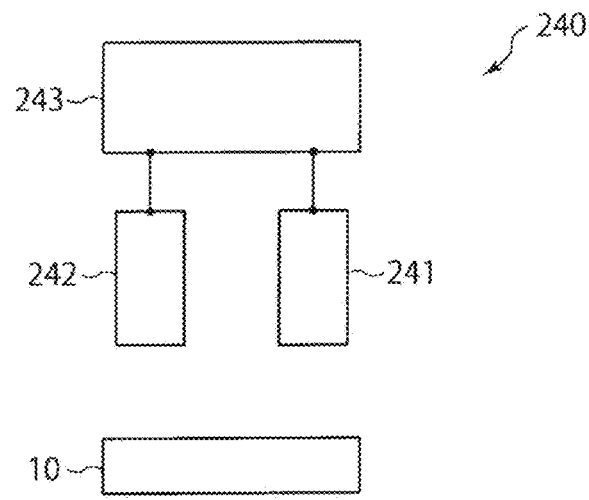
FIG. 12 is a schematic side view illustrating the configuration of a cell morphology observation part.

The cell morphology observation part 240 performs a cell morphology observation process with respect to the culture container 10. The cell morphology observation part 240 is, for example, an electronic camera module for observing the morphology of the cells existing in the culture container 10. A configuration example of the cell morphology observation part 240 is illustrated in FIG. 12. As illustrated in FIG. 12, the cell morphology observation part 240 includes an micro-observation-based imaging part 241 configured to image the morphology of the cells existing in the culture container 10 through the use of a transmission microscope (e.g., a phase-contrast microscope), a macro-observation-based imaging part 242 configured to comprehensively image the whole cells existing in the culture container 10, and an image processing part 243 configured to create image data for the determination of a cell state by processing the images taken by the micro-observation-based imaging part 241 and the macro-observation-based imaging part 242. The image processing part 243 creates, for example, a differential-filter-processed image (differential image) of an image of a colony formed by pluripotent stem cells. The image data created by the image processing part 243 are stored in the storage part 430 in association with the observation time.

The medium replacement part 250 performs a medium replacement process with respect to the culture container 10. In the medium replacement process, the medium replacement part 250 replaces the medium existing in the culture container 10 with a new medium. In the case where the medium replacement process is performed after the end of the incubation process, the medium existing in the culture container 10, which is replaced by a new medium, is an incubation-processed medium (hereinafter also referred to as a "used medium"). In the case where the medium replacement process is performed before the start of the incubation process, the medium existing in the culture container 10, which is replaced by a new medium, is a medium not subjected to the incubation process. In the case where the medium replacement process is performed after the cell separation process, the unnecessary cells separated from the culture container 10 in the cell separation process (e.g., the differentiation-started cells) are removed from the culture container 10 in the medium replacement process. Accordingly, if the medium replacement process is performed after the cell separation process, the medium replacement part 250 and the cell separation part 260 serve as a cell removal part configured to perform a cell removal process of removing the unnecessary cells from the culture container 10.

Figure 13:
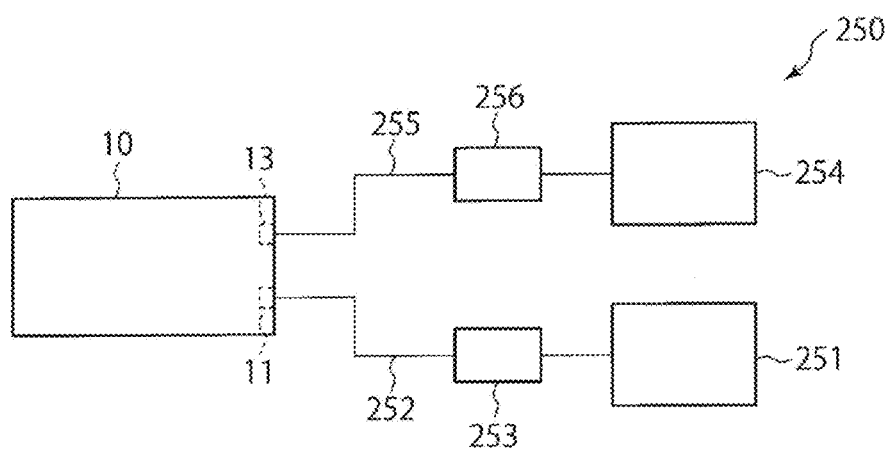
FIG. 13 is a schematic plan view illustrating the configuration of a medium replacement part.

A configuration example of the medium replacement part 250 is illustrated in FIG. 13. As illustrated in FIG. 13, the medium replacement part 250 includes a medium supply tank 251 configured to store a fresh medium not used in the incubation process, an inflow conduit 252 connectable at one end to the inlet port 11 of the culture container 10 and connected at the other end to the medium supply tank 251, a flow rate regulator 253 such as a valve, a pump or the like installed in the inflow conduit 252, a cell recovery tank 254, an outflow conduit 255 connectable at one end to the outlet port 13 of the culture container 10 and connected at the other end to the cell recovery tank 254, and a flow rate regulator 256 such as a valve, a pump or the like installed in the outflow conduit 255.

The medium replacement part 250 supplies a fresh medium stored in the medium supply tank 251 to the culture container 10 via the inflow conduit 252 connected to the inlet port 11 of the culture container 10. If the fresh medium is supplied to the culture container 10, the old medium existing in the culture container 10 (e.g., the incubation-processed medium) flows out from the outlet port 13 of the culture container 10. The medium replacement part 250 causes the medium recovery tank 254 to recover the medium flowing out from the outlet port 13 of the culture container 10 (e.g., the incubation-processed medium) through the outflow conduit 255 connected to the outlet port 13 of the culture container 10.

The incubation-processed medium recovered in the medium replacement part 250 is analyzed by the first medium analysis part 291 and the second medium analysis part 292. The first medium analysis part 291 performs a first medium analysis process of analyzing components of the incubation-processed medium recovered in the medium replacement part 250 and calculating a variation value of an extracellular metabolite. The kind of the extracellular metabolite is not particularly limited and may be at least one extracellular metabolite selected from a group consisting of L-glutamic acid, L-alanine and ammonia. The second medium analysis pan 292 performs a second medium analysis process of analyzing a time-dependent change in the variation value of the extracellular metabolite based on the variation value of the extracellular metabolite calculated in the first medium analysis process performed twice or more.

The cell separation part 260 performs a cell separation process with respect to the culture container 10. In the cell separation process, the cell separation part 260 selectively separates the unnecessary cells (e.g., the differentiation-started cells) existing in the culture container 10. The cells to be separated are identified based on the observation result of the cell morphology observation process.

Figure 14:
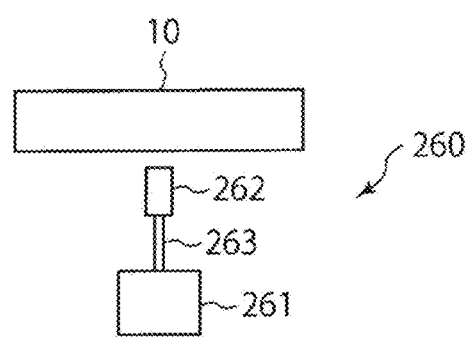
FIG. 14 is a schematic side view illustrating the configuration of a cell separation part.

A configuration example of the cell separation part 260 is illustrated in FIG. 14. As illustrated in FIG. 14, the cell separation part 260 includes a light source 261 configured to irradiate visible light onto the culture container 10, a light-receiving part 262 such as a lens or the like configured to converge the light, and an optical fiber 263 configured to supply the light from the light source 261 to the light-receiving part 262. The cell separation part 260 may selectively separate target cells from the culture container 10 by irradiating visible light onto the cells to be separated. The light source 261 is, for example, a light source configured to irradiate light having a wavelength of 400 to 500 nm, specifically, a laser light source or an LED light source (e.g., a laser light source or an LED light source configured to irradiate light having a wavelength of 405 nm, 420 nm or 450 nm). The output of the light source 261 is not particularly limited. For example, from the viewpoint of giving a light irradiation amount required in cell separation for a short period of time (e.g., 10 minutes or less), it is preferred that the light source 261 has an output of 100 mW or more.

In the present embodiment, the cell separation process is performed using the light. However, the cell separation process may be performed using ultrasonic waves. In the case of using ultrasonic waves, the cell separation part 260 includes an ultrasonic probe having a vibrator configured to ultrasonically vibrate in an up-down direction (predetermined direction). In this case, the cell separation part 260 can selectively separate target cells from the culture container 10 by bringing the ultrasonically-vibrating vibrator into contact with a point of the flat plate 32 of the culture container 10 at which the cells to be separated are located.

The cell recovery part 270 performs a cell recovery process with respect to the culture container 10. In the cell recovery process, the cell recovery part 270 separates the cells existing in the culture container 10 from the culture container 10 and recovers the separated cells.

Figure 15:
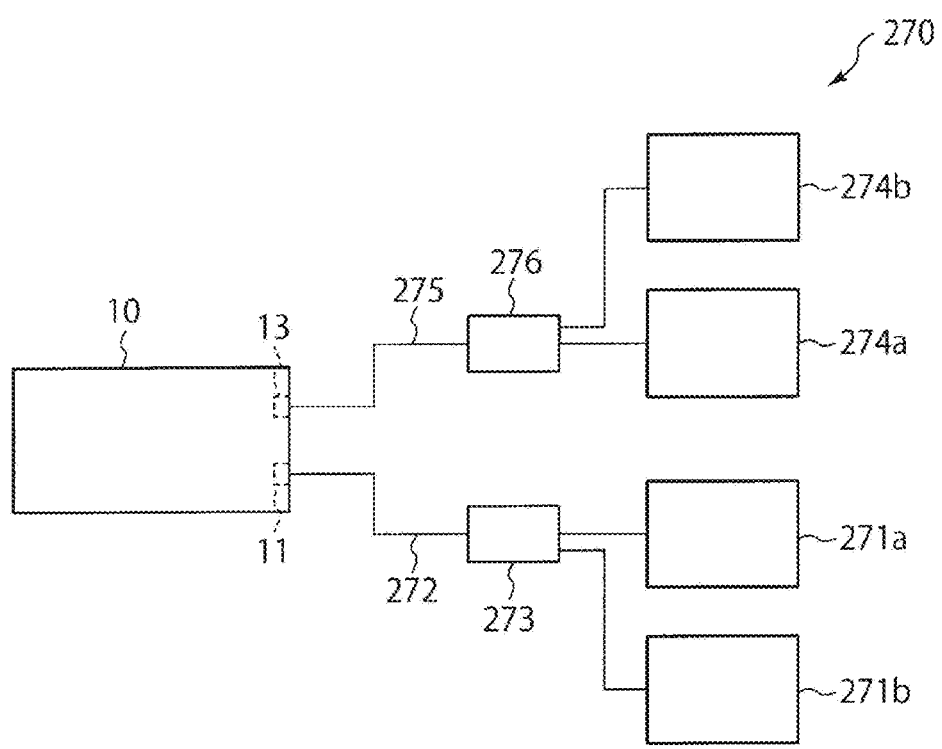
FIG. 15 is a schematic plan view illustrating the configuration of a cell recovery part.

A configuration example of the cell recovery part 270 is illustrated in FIG. 15. As illustrated in FIG. 15, the cell recovery part 270 includes a separation agent solution supply lank 271a configured to store a separation agent solution, a medium supply tank 271b configured to store a fresh medium, an inflow conduit 272 connectable at one end to the inlet port 11 of the culture container 10 and connected at the other end to the separation agent solution supply tank 271a and the medium supply tank 271b, a flow rate regulator 273 such as a valve, a pump or the like installed in the inflow conduit 272, a separation agent solution recovery tank 274a, a cell recovery tank 274b, an outflow conduit 275 connectable at one end to the outlet part 13 of the culture container 10 and connected at the other end to the separation agent solution recovery tank 274a and the cell recovery tank 274b, and a flow rate regulator 276 such as a valve, a pump or the like installed in the outflow conduit 275. The liquid (the separation agent solution or the fresh medium) to be supplied to the culture container 10 is selected by a switching valve of the flow rate regulator 273. The liquid (the separation agent solution or the cell-containing medium) recovered from the culture container 10 is selected by a switching valve of the flow rate regulator 276.

The cell recovery part 270 supplies the separation agent solution stored in the separation agent solution supply tank 271a to the culture container 10 through the inflow conduit 272 connected to the inlet port 11 of the culture container 10. If the separation agent solution is supplied to the culture container 10, the cells existing in the culture container 10 are separated from the culture container 10. The cell recovery part 270 causes the separation agent solution recovery tank 274a to recover the separation agent solution flowing out from the outlet port 13 of the culture container 10 through the outflow conduit 275 connected to the outlet port 13 of the culture container 10. Thereafter, the cell recovery part 270 supplies the fresh medium stored in the medium supply tank 271b to the culture container 10 through the inflow conduit 272 connected to the inlet port 11 of the culture container 10. If the fresh medium is supplied to the culture container 10, the separated cells are pushed by the fresh medium to flow out from the outlet port 13 together with the fresh medium. The cell recovery part 270 causes the cell recovery tank 274b to recover the cell-containing medium flowing out from the outlet port 13 of the culture container 10 through the outflow conduit 275 connected to the outlet port 13 of the culture container 10.

The container transfer part 280 transfers the container such as the culture container 10 or the like within the cell processing part 200 and performs delivery of the container such as the culture container 10 or the like between one operation part and another operation part. The container transfer part 280 includes a transfer path extending in a predetermined direction and a transfer arm installed in the transfer path. The respective operation parts are installed adjacent to the transfer path. The transfer arm may gain access to the interior of one operation part, unload the container from one operation part, transfer the unloaded container along the transfer path, gain access to the interior of another operation part, and load the container into another operation part. The transfer arm is provided with, for example, a holding mechanism configured to hold the container and is configured to move in the horizontal direction and the vertical direction and to turn about a vertical axis.

The control part 300 is a computer configured to generally control the operation of the cell culture apparatus 100 and to manage the respective processes in the cell culture apparatus 100 on a container-by-container basis. The control pan 300 is composed of, for example, a CPU, a RAM, a ROM and the like, and is configured to perform various kinds of processes based on various kinds of data, various kinds of programs and the like stored in the storage part 430. At this time, the control part 300 serves as an operation control part 310, a first determination part 320, a second determination part 330 or an observation condition adjustment part 340.

The operation control pan 310 controls various kinds of operation parts and executes various kinds of processes according to a process schedule stored in the storage part 430. For example, the operation control part 310 controls the operations of the incubation pan 230, the medium replacement part 250 and the first medium analysis part 291 so that the incubation process, the medium replacement process and the first medium analysis process are repeatedly performed twice or more with respect to the culture container 10 accommodating a certain medium. For example, when the incubation process, the medium replacement process and the first medium analysis process are repeatedly performed k times (where k is an integer of two or more) with respect to the culture container 10 accommodating a certain medium, a first-round incubation process, a first-round medium replacement process, a first-round first medium analysis process, a second-round incubation process, a second-round medium replacement process, a second-round first medium analysis process, . . . , a k-round incubation process, a k-round medium replacement process and a k-round first medium analysis process are sequentially performed.

The first determination part 320 performs a first determination process for determining whether the cells existing in the culture container 10 are in an undifferentiated state, based on an observation result (an observation image and/or a processed image thereof) obtained in the cell morphology observation process The second determination part 330 performs a second determination process for determining whether the cells existing in the culture container 10 are in an undifferentiated state, based on a time-dependent change in a variation value of an extracellular metabolite calculated in the first medium analysis process and/or in a variation value of an extracellular metabolite analyzed in the second medium analysis process.

The observation condition adjustment part 340 adjusts an observation condition in the cell morphology observation process based on a determination result obtained in the second determination process. For example, if it is determined in the second determination process that the cells existing in the culture container 10 are in an undifferentiated state, the observation condition adjustment part 340 increases the observation magnification, the number of observation times, the number of observation points or the like in order to enhance the observation sensitivity in a subsequent cell morphology observation process.

The input part 410 is composed of a pointing device such as a keyboard, a mouse or the like which is operated by an operator. The input part 410 inputs various kinds of operation signals such as an instruction from an operator (e.g., a process star instruction, a process result display instruction or the like), an input of data required in the respective processes and the like. The inputted data are stored in the storage part 430 by the control part 300.

The output part 420 is composed of, for example, a display or the like. The output part 420 outputs the results acquired or analyzed by various kinds of means (e.g., the observation result of an observation image or the like, or the analysis result of a variation value of an extracellular metabolite, a time-dependent change thereof or the like).

The storage part 430 is composed of, for example, a storage such as a RAM, a hard disk or the like. The storage part 430 stores various kinds of data, various kinds of programs and the like. In the storage part 430, there are stored, for example, attribute information of the culture container (e.g., the kind of cells, the kind of a medium, the history of subculture, and the like) and information such as an incubation process condition (e.g., a temperature or the like), an incubation process schedule (e.g., the start time of the incubation process, the end time of the incubation process or the like), a cell morphology observation condition (e.g., the observation interval, the observation magnification, the number of observation times, the number of observation points, imaging conditions or the like), a determination condition (e.g., a reference range) applied when performing various kinds of determination, and the like.

The notification part 440 outputs a warning to the outside, for example, when it is determined that the cells existing in the culture container 10 are in a poor state (e.g., a differentiation-started state). For example, the notification part 440 outputs a warning indication to the output part 420.

Hereinafter, embodiments of a cell culture processing procedure performed by the cell culture apparatus 100 will be described with reference to FIGS. 16 to 21.

<First Embodiment>

Figure 16:
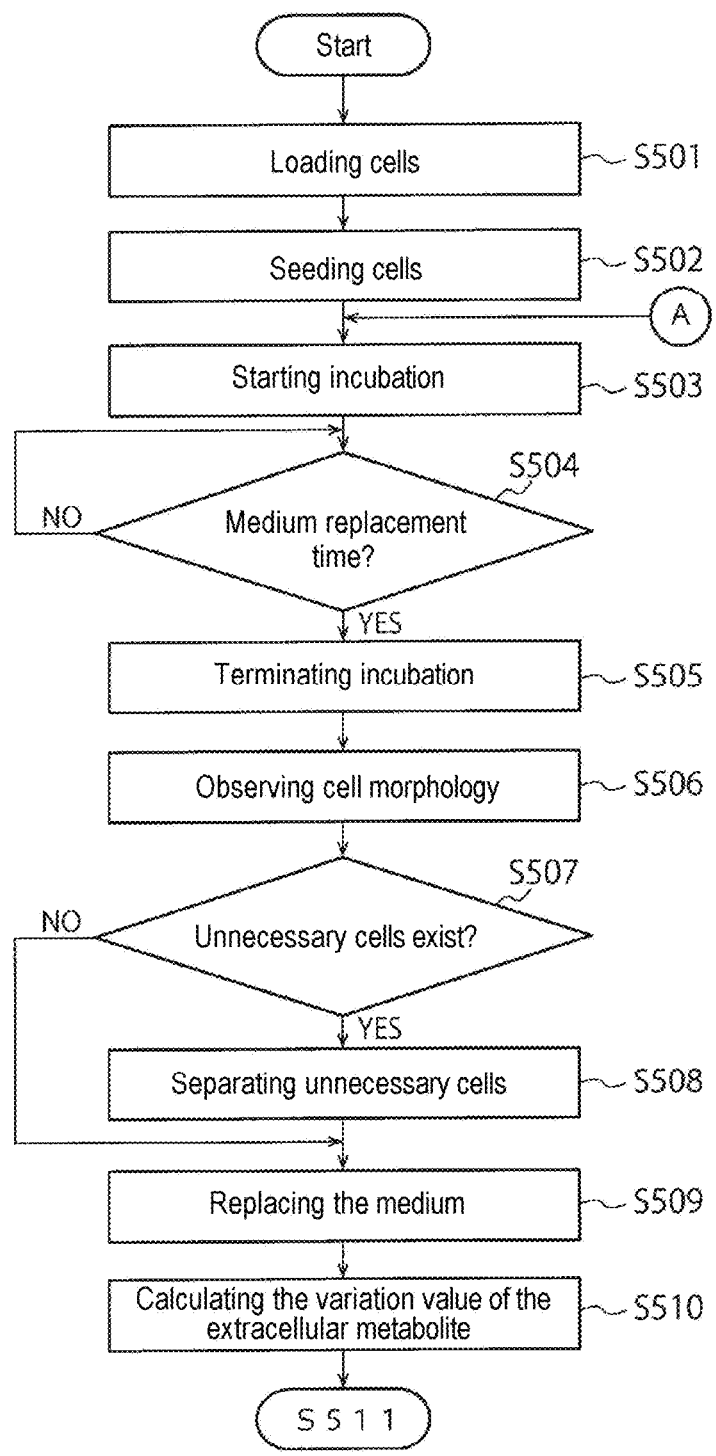
FIG. 16 is a flowchart illustrating a cell culture processing procedure (first embodiment) performed by the cell culture apparatus according to one embodiment of the present disclosure.
Figure 17:
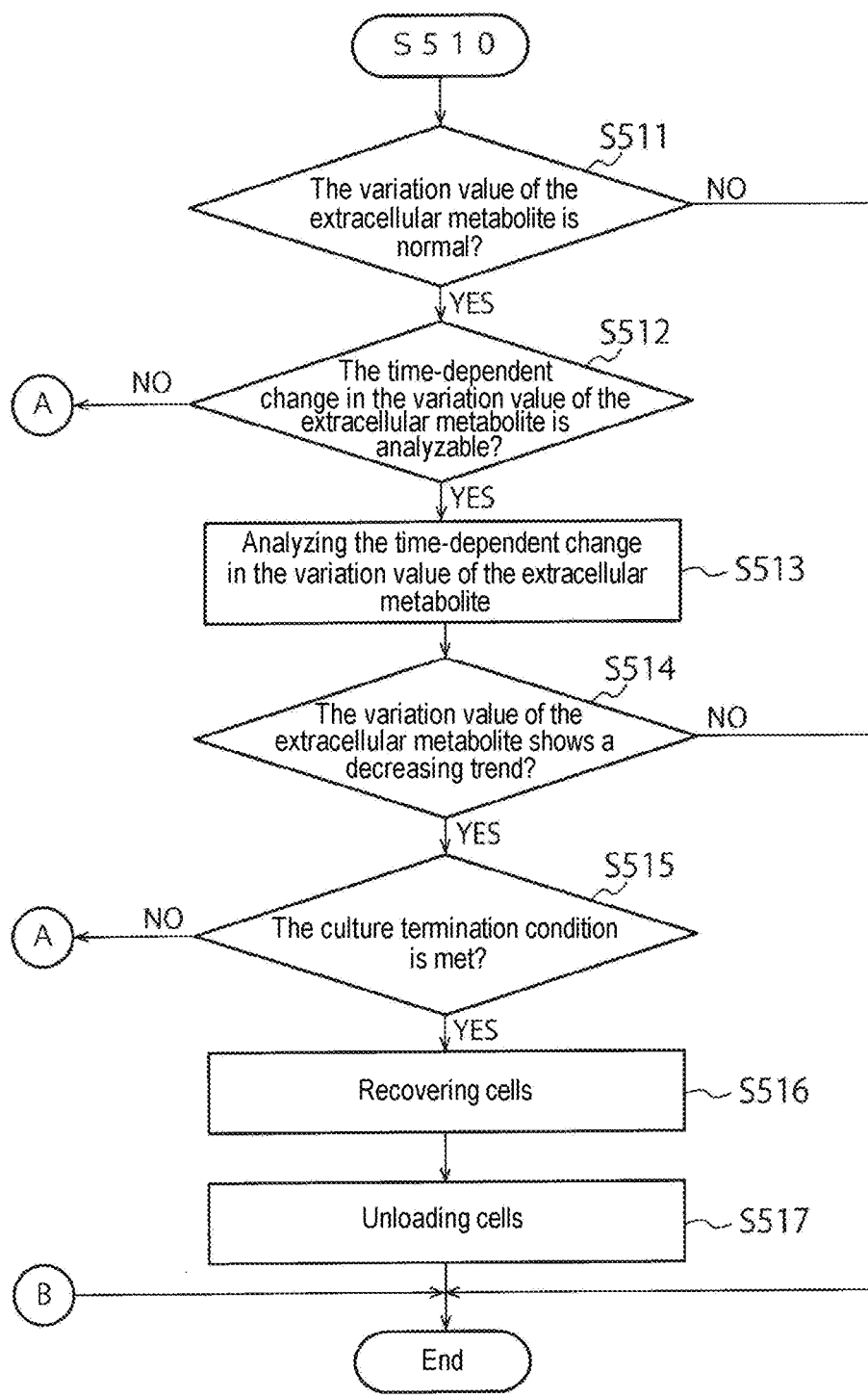
FIG. 17 is a flowchart illustrating the cell culture processing procedure (first embodiment) performed by the cell culture apparatus according to one embodiment of the present disclosure (FIG. 16 continued).

First, a first embodiment of a cell culture processing procedure performed by the cell culture apparatus 100 will be described with reference to FIGS. 16 and 17. FIGS. 16 and 17 are flowcharts illustrating a first embodiment of a cell culture processing procedure performed by the cell culture apparatus 100.

If a start instruction from an operator is inputted from the input part 410, the operation control part 310 controls the container loading/unloading part 210 to execute a cell loading process (step S501). In the cell loading process, a container accommodating cells (pluripotent stem cells of an undifferentiated state) to be cultured is loaded from outside of the cell culture apparatus 100 into the container loading/unloading part 210.

After step S501, the operation control part 310 controls the container transfer part 280 to transfer the container loaded into the container loading/unloading part 210 to the cell seeding part 220. Then, the operation control part 310 controls the cell seeding part 220 to execute a cell seeding process (step S502). In the cell seeding process, the cells (pluripotent stem cells of an undifferentiated state) to be cultured are seeded in a new culture container 10 not used in the cell culture. At this time, cells and a new medium not used in an incubation process are accommodated in the culture container 10.

After step S502, the operation control part 310 controls the container transfer part 280 to transfer the culture container 10 accommodating the pluripotent stem cells of an undifferentiated state and a fresh medium from the cell seeding part 220 to the incubation part 230. Then, the operation control part 310 controls the incubation part 230 to start an incubation process with respect to the culture container 10 (step S503). By referring to the incubation process condition stored in the storage part 430, the operation control part 310 controls the incubation part 230 so that the incubation process is realized under a predetermined condition suitable for cell culture. In the incubation process, the culture container 10 is kept under an environment suitable for cell culture and the cells existing in the culture container 10 are cultivated and proliferated.

After step S503, the operation control pan 310 determines whether the current time is a medium replacement time, by referring to the incubation process schedule stored in the storage part 430 (step S504). The medium replacement time is, for example, a time elapsed by a predetermined time period (e.g., 24 hours) from the start of the incubation process.

If it is determined that the current time is not the medium replacement time (if NO at step S504), the operation control part 310 continues to perform the incubation process. The operation control part 310 continues to perform the incubation process until it is determined that the current time is the medium replacement time.

If it is determined that the current time is the medium replacement time (if YES at step S504), the operation control part 310 terminates the incubation process (step S505) and proceeds to a cell morphology observation process (step S506).

After step S505, the operation control part 310 controls the container transfer part 280 to transfer the culture container 10 subjected to the incubation process in the incubation part 230 to the cell morphology observation part 240. Then, the operation control part 310 controls the cell morphology observation part 240 to execute a cell morphology observation process with respect to the culture container 10 (step S506). In the cell morphology observation process, the cell morphology observation and the taking of an observation image are performed by the micro-observation-based imaging part 241, and the cell morphology observation and the taking of an observation image are performed by the macro-observation-based imaging part 242. The observation images thus taken are processed by the image processing part 243 so that the observation images become suitable for the determination of a cell state. The image suitable for the determination of a cell state is, for example, a differential-filter-processed image (differential image) of an image of a colony. The observation image taken by the micro-observation-based imaging part 241 and the processed image thereof are mainly used to determine the state of cells contained in each colony. The observation image taken by the macro-observation-based imaging part 242 and the processed image thereof are mainly used to identify the position of a colony containing unnecessary cells (e.g., differentiation-started cells, cells of a poor growth state or the like). The operation control pan 310 causes the observation image and the processed image thereof to be stored in the storage part 430 in association with the observation time.

After step S506, the first determination part 320 determines the state of cells existing in the culture container 10 based on the observation image and/or the processed image thereof stored in the storage part 430 and determines whether unnecessary cells (e.g., differentiation-started cells, cells of a poor growth state or the like) exist (step S507). For example, the first determination part 320 extracts a contour image of a certain colony based on the observation image and/or the processed image thereof stored in the storage part 430 and acquires shape information and area information of the colony based on the extracted contour image. Then, the first determination part 320 analyzes a degree at which the shape of the colony is deformed compared with a reference shape (e.g., a perfect circle) (a deformation degree of the shape of the colony with respect to the reference shape) based on the acquired shape information. When the deformation degree falls within a reference range, the first determination pan 320 determines that the cells contained in the colony are in an undifferentiated state. When the deformation degree falls outside the reference range, the first determination pan 320 determines that the cells contained in the colony are not in an undifferentiated state. Alternatively, the first determination part 320 analyzes whether the area of the colony falls within a reference range, based on the acquired area information. When the area of the colony falls within the reference range, the first determination part 320 determines that the cells contained in the colony are in an undifferentiated state. When the area of the colony falls outside the reference range, the first determination part 320 determines that the cells contained in the colony are not in an undifferentiated state. In some embodiments, the first determination part 320 determines whether the cells contained in the colony are in an undifferentiated state, based on the differential-filter-processed image (differential image) of the image of the colony and according to the method described in Japanese laid-open publication No. 2014-18184 cited above. In the case where the cell morphology observation process is performed twice or more with respect to the same culture container 10, the first determination part 320 may compare the observation image and/or the processed image thereof acquired in the current cell morphology observation process with the observation image and/or the processed image thereof acquired in the previous cell morphology observation process (specifically, in the immediately-previous cell morphology observation process). Based on a time-dependent change in the cell morphology, the first determination part 320 may determine whether the cells contained in the colony is in an undifferentiated state. If it is determined that a colony containing unnecessary cells (e.g., differentiation-started cells, cells of a poor growth state or the like) exists, the first determination part 320 identifies a position at which the colony containing unnecessary cells exists. The first determination part 320 stores the position information in the storage part 430.

If it is determined at step S507 by the first determination part 320 that the colony containing unnecessary cells exists (if YES at step S507), the operation control part 310 controls the container transfer part 280 to transfer the culture container 10 from the cell morphology observation part 240 to the cell separation part 260. Then, the operation control part 310 controls the cell separation part 260 to execute a cell separation process with respect to the culture container 10 (step S508). The operation control part 310 selectively separates the colony containing unnecessary cells, based on the position information of the colony containing unnecessary cells, which is stored in the storage part 430. The cells separated in the cell separation process are floating in the medium and are removed together with the old medium during a medium replacement process. After the cell separation process, the operation control part 310 controls the container transfer part 280 to transfer the culture container 10 from the cell separation part 260 to the medium replacement part 250 such that the medium replacement process is performed (step S509).

If it is determined at step S507 by the first determination part 320 that the colony containing unnecessary cells does exist (if NO at step S507), the operation control part 310 controlling the container transfer part 280 to transfer the culture container 10 from the cell morphology observation part 240 to the medium replacement part 250 such that the medium replacement process is performed (step S509).

After the culture container 10 is transferred to the medium replacement part 250, the operation control part 310 controls the medium replacement part 250 to execute the medium replacement process with respect to the culture container 10 (step S509). In the medium replacement process, the medium subjected to the incubation process in the culture container 10 is replaced with a fresh medium not used in the incubation process. The cells separated at step S508 are removed from the culture container 10 together with the incubation-processed medium. In the case where the medium replacement process is performed after the cell separation process, the medium replacement part 250 and the cell separation part 260 serve as a cell removal part.

After step S509, the operation control part 310 controls the first medium analysis part 291 to execute a first medium analysis process for calculating a variation value of an extracellular metabolite existing in the incubation-processed medium recovered in the medium replacement process (step S510). In the present embodiment, the extracellular metabolite is at least one selected from a group consisting of L-glutamic acid, L-alanine and ammonia. However, the extracellular metabolite, the variation value of which is analyzed by the first medium analysis part 291, may be other extracellular metabolites.

After step S510, the second determination part 330 determines whether the cells existing in the culture container 10 are in an undifferentiated state, based on the variation value of the extracellular metabolite calculated by the first medium analysis part 291, specifically, depending on whether the variation value of the extracellular metabolite is normal (step S511). When the variation value of the extracellular metabolite is normal, the second determination part 330 determines that the cells are in an undifferentiated state. When the variation value of the extracellular metabolite is not normal, the second determination part 330 determines that the cells are not in an undifferentiated state. When the variation value of the extracellular metabolite falls within a reference range, the second determination part 330 determines that the variation value of the extracellular metabolite is normal. When the variation value of the extracellular metabolite falls outside the reference range, the second determination part 330 determines that the variation value of the extracellular metabolite is not normal. For example, when the variation value of the extracellular metabolite is zero, the second determination part 330 determines that the variation value of the extracellular metabolite is not normal.

If it is determined at step S511 by the second determination part 330 that the variation value of the extracellular metabolite is not normal (namely, the cells are not in an undifferentiated state) (if NO at step S511), the operation control part 310 stops the process with respect to the culture container 10. At this time, the notification part 440 outputs a warning to the outside. For example, the notification part 440 outputs a warning indication to the output part 420.

If it is determined at step S511 by the second determination part 330 that the variation value of the extracellular metabolite is normal (namely, the cells are in an undifferentiated state) (if YES at step S511), the operation control part 310 determines whether a time-dependent change in the variation value of the extracellular metabolite is analyzable (step S512).

When the variation value of the extracellular metabolite existing in the incubation-processed medium recovered in the current medium replacement process is normal and the variation value of the extracellular metabolite existing in the incubation-processed medium recovered in the previous medium replacement process (specifically, in the immediately-previous medium replacement process) is normal, the operation control part 310 determines that the time-dependent change in the variation value of the extracellular metabolite is analyzable.

In order to analyze the time-dependent change in the variation value of the extracellular metabolite, it is necessary to compare the variation value of the extracellular metabolite existing in the incubation-processed medium recovered in the current medium replacement process with the variation value of the extracellular metabolite existing in the incubation-processed medium recovered in the previous medium replacement process (specifically, in the immediately-previous medium replacement process). In order to accurately perform the comparison, it is required that the time periods of the incubation processes performed with respect to two incubation-processed media to be compared are equal to each other. In the present embodiment, the incubation-processed media recovered in any medium replacement process meet this requirement.

If it is determined at step S512 that the time-dependent change in the variation value of the extracellular metabolite is not analyzable (if NO at step S512), the operation control part 310 controls the container transfer part 280 to transfer the culture container 10 from the medium replacement part 250 to the incubation part 230 and controls the incubation part 230 to start an incubation process with respect to the culture container 10 accommodating a fresh medium not subjected to the incubation process (step S503). The operation control part 310 repeats a series of processes of step S503 to step S512 until it is determined that the time-dependent change in the variation value of the extracellular metabolite is analyzable.

If it is determined at step S512 that the time-dependent change in the variation value of the extracellular metabolite is analyzable (if YES at step S512), the operation control part 310 controls the second medium analysis part 292 to execute a second medium analysis process for analyzing the time-dependent change in the variation value of the extracellular metabolite (step S513). The second medium analysis part 292 compares the variation value of the extracellular metabolite existing in the incubation-processed medium recovered in the current medium replacement process with the variation value of the extracellular metabolite existing in the incubation-processed medium recovered in the previous medium replacement process (specifically, in the immediately-previous medium replacement process) according to the control of the operation control part 310, thereby analyzing the time-dependent change in the variation value of the extracellular metabolite. The time-dependent change in the variation value of the extracellular metabolite is acquired as, for example, a decreasing trend, an increasing trend, or no increase/decrease (little increase/decrease).

After step S513, the second determination pan 330 determines whether the cells are in an undifferentiated state, based on the time-dependent change in the variation value of the extracellular metabolite, specifically, depending on whether the variation value of the extracellular metabolite shows a decreasing trend (step S514). In the present embodiment, the extracellular metabolite, namely at least one selected from a group consisting of L-glutamic acid. L-alanine and ammonia, serves as an indicator which indicates that the pluripotent stem cells are in an undifferentiated state, when the time-dependent change in the variation value thereof shows a decreasing trend. However, when other extracellular metabolite is used as an indicator, depending on the kind of extracellular metabolites, there may be a case where the extracellular metabolite serves as an indicator which indicates that the pluripotent stem cells are in an undifferentiated state, when the time-dependent change in the variation value of the extracellular metabolite shows an increasing trend.

The second determination part 330 determines that the cells are in an undifferentiated state, when the time-dependent change in the variation value of the extracellular metabolite shows a decreasing trend, and determines that the cells are not in an undifferentiated state, when the time-dependent change in the variation value of the extracellular metabolite shows a trend other than the decreasing trend (an increasing rend, no increase/decrease or the like).

If it is determined at step S514 by the second determination part 330 that the time-dependent change in the variation value of the extracellular metabolite does not show a decreasing trend (namely, the cells are not in an undifferentiated state) (if NO at step S514), the operation control part 310 stops the process with respect to the culture container 10. At this time, the notification part 440 outputs a warning to the outside. For example, the notification part 440 outputs a warning indication to the output part 420.

If it is determined at step S514 by the second determination part 330 that the time-dependent change in the variation value of the extracellular metabolite shows a decreasing trend (namely, the cells are in an undifferentiated state) (if YES at step S514), the operation control part 310 determines whether the culture container 10 meets a culture termination condition (step S515). Examples of the culture termination condition may include a condition that the number of cells existing in the culture container 10 is equal to or larger than a threshold value (the cells are in a confluent state or a state close to the confluent state), a condition that the incubation process is performed for a predetermined time, and the like. In the case where the number of cells existing in the culture container 10 is used as the culture termination condition, the operation control part 310 analyzes the number of cells existing in the culture container 10 based on the observation image and/or the processed image thereof acquired in the cell morphology observation process.

If it is determined at step S515 that the culture container 10 does not meet the culture termination condition (if NO at step S515), the operation control part 310 controls the container transfer part 280 to transfer the culture container 10 from the medium replacement part 250 to the incubation part 230, and controls the incubation part 230 to start an incubation process with respect to the culture container 10 accommodating a fresh medium not subjected to the incubation process (step S503). The operation control part 310 repeatedly executes a series of processes of step S503 to step S515 until it is determined that the culture container 10 meets the culture termination condition.

If it is determined at step S515 that the culture container 10 meets the culture termination condition (if YES at step S515), the operation control part 310 controls the container transfer part 280 to transfer the culture container 10 from the medium replacement part 250 to the cell recovery part 270. Then, the operation control part 310 controls the cell recovery part 270 to execute a cell recovery process with respect to the culture container 10 (step S516). In the cell recovery process, the cells are recovered from the culture container 10 and are accommodated in another container.

After step S316, the operation control part 310 controls the container transfer part 280 to transfer the container, which accommodates the cells recovered from the culture container 10, from the cell recovery part 270 to the container loading/unloading part 210. Then, the operation control part 310 controls the container loading/unloading part 210 to unload the container to outside of the cell culture apparatus 100 (step S517).

After step S516, the operation control part 310 controls the container transfer part 280 to transfer the container, which accommodates the cells recovered from the culture container 10, from the cell recovery part 270 to the cell seeding part 220. Then, the operation control part 310 may control the cell seeding part 220 to seed the cells existing in the container in a new culture container 10 and to execute a subculture process. In this case, the processes executed after the cell seeding process are performed in the same manner as described above.

<Second Embodiment>

Figure 18:
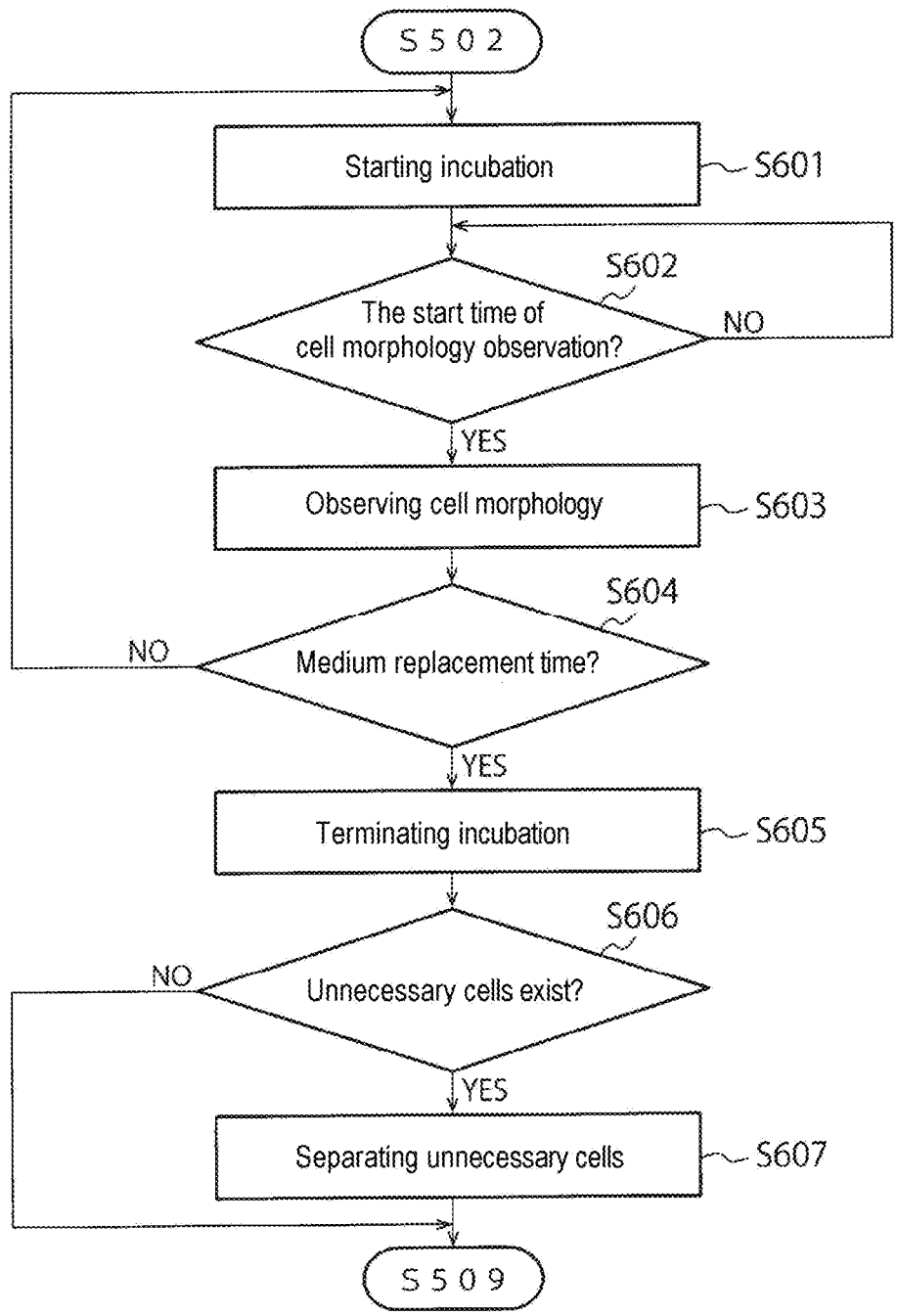
FIG. 18 is a flowchart illustrating a cell culture processing procedure (second embodiment) performed by the cell culture apparatus according to one embodiment of the present disclosure.

Next, a second embodiment of a cell culture processing procedure performed by the cell culture apparatus 100 will be described with reference to FIG. 18. FIG. 18 is a flowchart illustrating a second embodiment of a cell culture processing procedure performed by the cell culture apparatus 100. The respective processes of the second embodiment are executed in the same manner as described in the first embodiment, unless specifically mentioned otherwise.

In the second embodiment, processes of step S502 and previous steps in the first embodiment are executed in the same manner as described in the first embodiment.

After step S502, the operation control part 310 controls the container transfer part 280 to transfer the culture container 10 from the cell seeding part 220 to the incubation part 230. Then, the operation control part 310 controls the incubation part 230 to start an incubation process with respect to the culture container 10 (step S601).

After step S601, the operation control part 310 determines whether the current time is the start time of the cell morphology observation process, by referring to the cell morphology observation schedule stored in the storage pan 430 (step S602). Examples of the start time of the cell morphology observation process may include a time elapsed by a predetermined time period (e.g., 6, 12, 18 or 24 hours) after the start of the incubation process. For example, the start time of the cell morphology observation process is set so that the cell morphology observation process is performed multiple times at predetermined intervals (e.g., at 6-hour intervals) during the time period from the start of the incubation process to the medium replacement process (e.g., for 24 hours after the start of the incubation process).

If it is determined at step S602 that the current time is not the start time of the cell morphology observation process (if NO at step S602), the operation control part 310 continues to perform the incubation process performed by the incubation part 230. If it is determined at step S602 that the current time is the start time of the cell morphology observation process (if YES at step S602), the operation control part 310 stops the incubation process performed by the incubation part 230. The operation control pan 310 controls the container transfer part 280 to transfer the culture container 10 from the incubation pan 230 to the cell morphology observation part 240. Then, the operation control part 310 controls the cell morphology observation part 240 to execute a cell morphology observation process with respect to the culture container 10 (step S603).

After step S603, the operation control part 310 determines whether the current time is the medium replacement time, by referring to the incubation process schedule stored in the storage part 430 (step S604). The medium replacement time may be, for example, a time elapsed by a predetermined time period (e.g., 24 hours) from the start of the incubation process.

If it is determined at step S604 that the current time is not the medium replacement time (if NO at step S604), the operation control part 310 controls the container transfer part 280 to transfer the culture container 10 from the cell morphology observation part 240 to the incubation part 230, and controls the incubation part 230 to resume the interrupted incubation process with respect to the culture container 10 (step S601). The operation control part 310 repeatedly executes a series of processes of step S601 to S604 until it is determined that the current time is the medium replacement time.

If it is determined that the current time is the medium replacement time (if YES at step S604), the operation control part 310 terminates the incubation process (step S605) and proceeds to step S606.

After step S605, the first determination part 320 determines whether a colony containing unnecessary cells (e.g., differentiation-started cells, cells of a poor growth state or the like) exists in the culture container 10, based on the observation image and/or the processed image thereof stored in the storage part 430 (step S606). In the case where the cell morphology observation process is performed twice or more during a period of time from the start of the incubation process to the end of the incubation process, the first determination part 320 determines whether a colony containing unnecessary cells exists, based on the observation images taken during all cell morphology observation processes and/or the processed images thereof. If it is determined that the colony containing unnecessary cells exists, the first determination part 320 identifies a position at which the colony containing unnecessary cells exists and stores the respective position information in the storage part 430.

If it is determined at step S606 by the first determination part 320 that the colony containing unnecessary cells exists (if YES at step S606), the operation control part 310 controls the container transfer part 280 to transfer the culture container 10 from the cell morphology observation part 240 to the cell separation part 260. Then, the operation control part 310 controls the cell separation part 260 to execute a cell separation process with respect to the culture container 10 (step S607). After step S607, the operation control part 310 controls the container transfer part 280 to transfer the culture container 10 from the cell separation part 260 to the medium replacement part 250 and controls the medium replacement par 250 to perform the medium replacement process (step S509).

If it is determined at step S606 by the first determination part 320 that the colony containing unnecessary cells does not exist (if NO at step S606), the operation control part 310 controls the container transfer part 280 to transfer the culture container 10 from the cell morphology observation part 240 to the medium replacement part 250, and controls the medium replacement part 250 to perform the medium replacement process (step S509).

The processes of step S509 and subsequent steps in the second embodiment are the same as those of the first embodiment.

In the second embodiment, the cell morphology observation process can be performed twice or more during the period of time from the start of the incubation process to the end of the incubation process. When adjusting the observation condition of the cell morphology observation process based on the determination result obtained in the second determination process, the observation condition adjustment part 340 can adjust the number of the cell morphology observation processes performed from the start of the incubation process to the end of the incubation process. For example, if it is determined in the second determination process that the cells existing in the culture container 10 are in an undifferentiated state, the observation condition adjustment pan 340 increases the number of the cell morphology observation processes performed from the start of the incubation process to the end of the incubation process. Additionally or alternatively, it may be possible to increase the observation magnification, the number of observation points or the like in the cell morphology observation processes performed from the start of the incubation process to the end of the incubation process.

<Third Embodiment>

Figure 19:
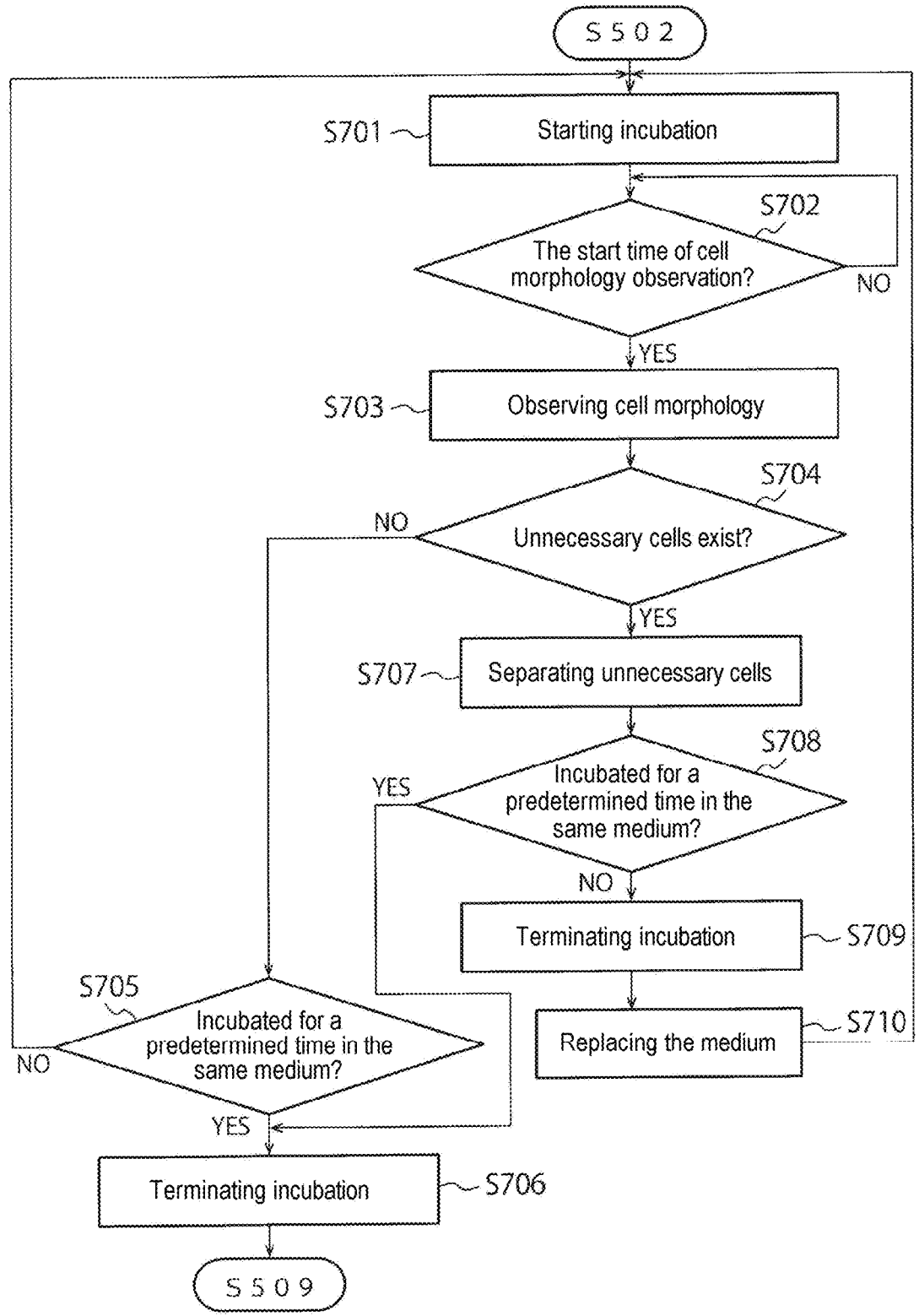
FIG. 19 is a flowchart illustrating a cell culture processing procedure (third embodiment) performed by the cell culture apparatus according to one embodiment of the present disclosure.

Next, a third embodiment of a cell culture processing procedure performed by the cell culture apparatus 100 will be described with reference to FIG. 19. FIG. 19 is a flowchart illustrating a third embodiment of a cell culture processing procedure performed by the cell culture apparatus 100. Respective processes of the third embodiment are executed in the same manner as described in the first embodiment, unless specifically mentioned otherwise.

In the third embodiment, the processes to step S502 and previous steps in the first embodiment are executed in the same manner as described in the first embodiment.

After step S502, the operation control part 310 controls the container transfer pan 280 to transfer the culture container 10 from the cell seeding part 220 to the incubation part 230. Then, the operation control part 310 controls the incubation part 230 to start an incubation process with respect to the culture container 10 (step S701).

After step S701, the operation control part 310 determines whether the current time is the start time of the cell morphology observation process, by referring to the cell morphology observation schedule stored in the storage part 430 (step S702). Examples of the start time of the cell morphology observation process may include a time elapsed by a predetermined time period (e.g., 6, 12, 18 or 24 hours) after the start of the incubation process. For example, the start time of the cell morphology observation process is set so that the cell morphology observation process is performed multiple times at predetermined intervals (e.g., at 6-hour intervals) during a period of time from the start of the incubation process to the medium replacement process (e.g., for 24 hours after the start of the incubation process).

If it is determined at step S702 that the current time is not the start time of the cell morphology observation process (if NO at step S702), the operation control part 310 controls the incubation part 230 to continuously perform the incubation process. If it is determined at step S702 that the current time is the start time of the cell morphology observation process (if YES at step S702), the operation control part 310 controls the incubation part 230 to stop the incubation process. The operation control pan 310 controls the container transfer part 280 to transfer the culture container 10 from the incubation part 230 to the cell morphology observation part 240. Then, the operation control part 310 controls the cell morphology observation part 240 to execute a cell morphology observation process with respect to the culture container 10 (step S703).

After step S703, the first determination part 320 determines whether a colony containing unnecessary cells (e.g., differentiation-started cells, cells of a poor growth state or the like) exists in the culture container 10, based on the observation image and/or the processed image thereof stored in the storage part 430 (step S704).

If it is determined at step S704 by the first determination part 320 that the colony containing unnecessary cells does not exist (if NO at step S704), the operation control part 310 determines whether the incubation process has been executed for a predetermined time in the same medium (step S705). If it is determined that the incubation process has not been executed for a predetermined time in the same medium (if NO at step S705), the operation control part 310 controls the container transfer part 280 to transfer the culture container 10 from the cell morphology observation part 240 to the incubation part 230, and controls the incubation part 230 to resume the interrupted incubation process with respect to the culture container 10 (step S701). If it is determined that the incubation process has been executed for a predetermined time in the same medium (if YES at step S705), the operation control part 310 controls the incubation part 230 to terminate the incubation process (step S706). The operation control part 310 controls the container transfer part 280 to transfer the culture container 10 from the cell morphology observation part 240 to the medium replacement part 250, and controls the medium replacement part 250 to perform the medium replacement process (step S509).

If it is determined at step S704 by the first determination part 320 that the colony containing unnecessary cells exists (if YES at step S704), the operation control part 310 controls the container transfer part 280 to transfer the culture container 10 from the cell morphology observation part 240 to the cell separation part 260. Then, the operation control part 310 controls the cell separation part 260 to execute a cell separation process with respect to the culture container 10 (step S707).

After step S707, the operation control part 310 determines whether the incubation process has been executed for a predetermined time in the same medium (step S708).

If it is determined at step S708 that the incubation process has not been executed for a predetermined time in the same medium (if NO at step S708), the operation control part 310 controls the incubation part 230 to terminate the incubation process (step S709). The operation control part 310 controls the container transfer part 280 to transfer the culture container 10 from the cell separation part 260 to the medium replacement part 250. Then, the operation control part 310 controls the medium replacement part 250 to execute the medium replacement process with respect to the culture container 10 (step S710).

After step S710, the operation control part 310 controls the container transfer part 280 to transfer the culture container 10 from the medium replacement part 250 to the incubation part 230. Then, the operation control part 310 controls the incubation part 230 to start the incubation process with respect to the culture container 10 accommodating a fresh medium not subjected to the incubation process (step S701).

If it is determined at step S708 that the incubation process has been executed for a predetermined time in the same medium (if YES at step S708), the operation control part 310 controls the incubation part 230 to terminate the incubation process (step S706). The operation control part 310 controls the container transfer part 280 to transfer the culture container 10 from the cell separation part 260 to the medium replacement part 250, and controls the medium replacement part 250 to execute the medium replacement process (step S509).

The processes of step S509 and subsequent steps in the third embodiment are the same as those of the first embodiment.

In the third embodiment, the cell morphology observation process can be performed twice or more during the period of time from the start of the incubation process to the end of the incubation process. When adjusting the observation condition of the cell morphology observation process based on the determination result obtained in the second determination process, the observation condition adjustment part 340 may adjust the number of the cell morphology observation processes performed from the start of the incubation process to the end of the incubation process. For example, if it is determined in the second determination process that the cells existing in the culture container 10 are in an undifferentiated state, the observation condition adjustment part 340 increases the number of the cell morphology observation processes performed from the star of the incubation process to the end of the incubation process. Additionally or alternatively, it may be possible to increase the observation magnification, the number of observation points or the like in the cell morphology observation processes performed from the start of the incubation process to the end of the incubation process.

<Fourth Embodiment>

Figure 20:
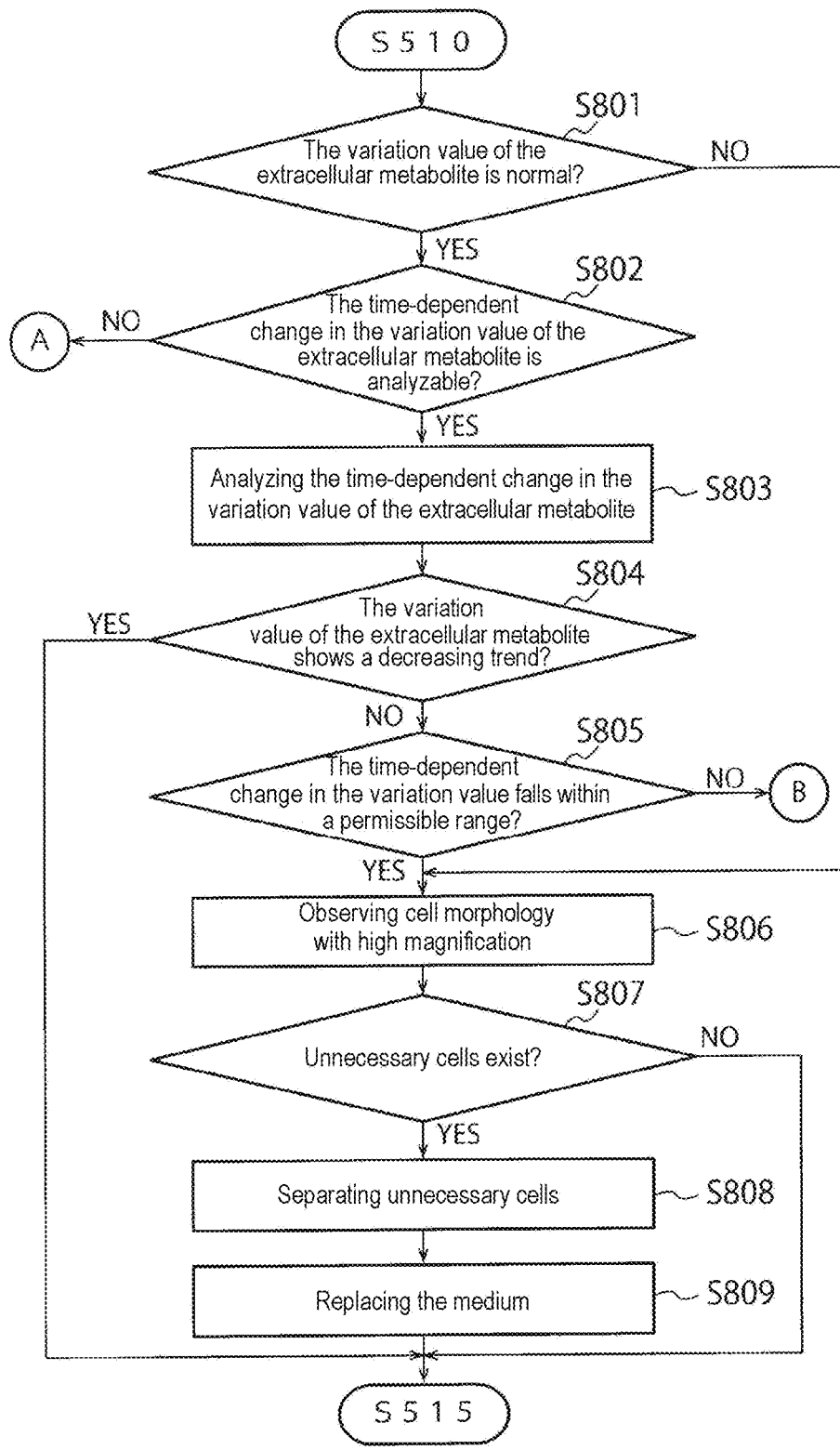
FIG. 20 is a flowchart illustrating a cell culture processing procedure (fourth embodiment) performed by the cell culture apparatus according to one embodiment of the present disclosure.

Next, a fourth embodiment of a cell culture processing procedure performed by the cell culture apparatus 100 will be described with reference to FIG. 20. FIG. 20 is a flowchart illustrating a fourth embodiment of a cell culture processing procedure performed by the cell culture apparatus 100. Respective processes of the fourth embodiment are executed in the same manner as described in the first embodiment, unless specifically mentioned otherwise.

In the fourth embodiment, the processes to step S502 and previous steps in the first embodiment are executed in the same manner as described in the first embodiment.

After step S510, the second determination part 330 determines whether the cells existing in the culture container 10 are in an undifferentiated state, based on the variation value of the extracellular metabolite calculated by the first medium analysis part 291, specifically, depending on whether the variation value of the extracellular metabolite is normal (step S801). When the variation value of the extracellular metabolite is normal, the second determination part 330 determines that the cells are in an undifferentiated state. When the variation value of the extracellular metabolite is not normal, the second determination part 330 determines that the cells are not in an undifferentiated state.

If it is determined at step S801 by the second determination part 330 that the variation value of the extracellular metabolite is not normal (namely, the cells are not in an undifferentiated state) (if NO at step S801), the operation control part 310 controls the container transfer pan 280 to transfer the culture container 10 from the medium replacement part 250 to the cell morphology observation part 240. Then, the operation control part 310 controls the cell morphology observation part 240 to execute a high-magnification cell morphology observation process with respect to the culture container 10 (step S806). At this time, the observation condition adjustment pan 340 adjusts the observation magnification in the cell morphology observation process to a high magnification.

If it is determined at step S801 by the second determination part 330 that the variation value of the extracellular metabolite is normal (namely, the cells are in an undifferentiated state) (if YES at step S801), the operation control part 310 determines whether the time-dependent change in the variation value of the extracellular metabolite is analyzable (step S802).

If it is determined at step S802 that the time-dependent change in the variation value of the extracellular metabolite is not analyzable (if NO at step S802), the operation control part 310 controls the container transfer part 280 to transfer the culture container 10 from the medium replacement part 250 to the incubation part 230, and controls the incubation part 230 to start the incubation process with respect to the culture container 10 accommodating a fresh medium not subjected to the incubation process (step S503).

If it is determined at step S802 that the time-dependent change in the variation value of the extracellular metabolite is analyzable (if YES at step S802), the operation control part 310 controls the second medium analysis part 292 to execute a second medium analysis process for analyzing the time-dependent change of the variation value of the extracellular metabolite (step S803).

After step S803, the second determination part 330 determines whether the cells are in an undifferentiated state, based on the time-dependent change in the variation value of the extracellular metabolite, specifically, depending on whether the variation value of the extracellular metabolite shows a decreasing trend (step S804). When the time-dependent change in the variation value of the extracellular metabolite shows a decreasing trend, the second determination part 330 determines that the cells are in an undifferentiated state. When the time-dependent change in the variation value of the extracellular metabolite shows a trend other than the decreasing trend (an increasing trend, no increase/decrease, or the like), the second determination part 330 determines that the cells are not in an undifferentiated state.

If it is determined at step S804 by the second determination part 330 that the lime-dependent change in the variation value of the extracellular metabolite shows a decreasing trend (namely, the cells are in an undifferentiated state) (if YES at step S804), the operation control part 310 proceeds to step S515.

If it is determined at step S804 by the second determination part 330 that the time-dependent change in the variation value of the extracellular metabolite does not show a decreasing trend (namely, the cells are not in an undifferentiated state) (if NO at step S804), the operation control part 310 determines whether the time-dependent change in the variation value of the extracellular metabolite falls within a permissible range (step S805). For example, if the time-dependent change in the variation value of the extracellular metabolite shows no increase or if the time-dependent change in the variation value of the extracellular metabolite shows a slightly increasing trend, the operation control part 310 determines that the time-dependent change in the variation value of the extracellular metabolite falls within a permissible range. If the time-dependent change in the variation value of the extracellular metabolite does not show a decreasing trend but falls within a permissible range, it is considered that, although the cells are not in an undifferentiated state, the degree of differentiation is small and the culture can be continuously performed by removing the differentiation-started cells.

If it is determined at step S805 by the second determination part 330 that the time-dependent change in the variation value of the extracellular metabolite does not fall within a permissible range (if NO at step S805), the operation control part 310 stops the process with respect to the culture container 10. At this time, the notification part 440 outputs a warning to the outside. For example, the notification part 440 outputs a warning indication to the output part 420.

If it is determined at step S805 by the second determination part 330 that the time-dependent change in the variation value of the extracellular metabolite falls within a permissible range (if YES at step S805), the operation control par 310 controls the container transfer part 280 to transfer the culture container 10 from the medium replacement part 250 to the cell morphology observation part 240, and controls the cell morphology observation part 240 to execute a high-magnification cell morphology observation process with respect to the culture container 10 (step S806). At this time, the observation condition adjustment part 340 adjusts the observation magnification in the cell morphology observation process to a high magnification. The high-magnification cell morphology observation process of step S806 is executed in the same manner as a typical cell morphology observation process except that the observation magnification is a high magnification.

After step S806, the first determination part 320 determines whether a colony containing unnecessary cells (e.g., differentiation-started cells, cells of a poor growth state or the like) exists in the culture container 10, based on the observation image and/or the processed image thereof stored in the storage part 430 (step S807).

If it is determined at step S807 by the first determination part 320 that the colony containing unnecessary cells does not exist (if NO at step S807), the operation control part 310 proceeds to step S515. If it is determined at step S807 by the first determination part 320 that the colony containing unnecessary cells exists (if YES at step S807), the operation control part 310 controls the container transfer part 280 to transfer the culture container 10 from the cell morphology observation part 240 to the cell separation part 260. Then, the operation control part 310 controls the cell separation part 260 to execute the cell separation process with respect to the culture container 10 (step S808).

After step S808, the operation control part 310 controls the container transfer part 280 to transfer the culture container 10 from the cell separation part 260 to the medium replacement part 250. Then, the operation control part 310 controls the medium replacement part 250 to perform the medium replacement process with respect to the culture container 10 (step S809). In the case where the medium replacement process is performed after the cell separation process, the medium replacement part 250 and the cell separation part 260 serve as a cell removal part. After step S809, the operation control part 310 proceeds to step S515.

The processes of step S515 and subsequent steps in the fourth embodiment are the same as those of the first embodiment.

<Fifth Embodiment>

Figure 21:
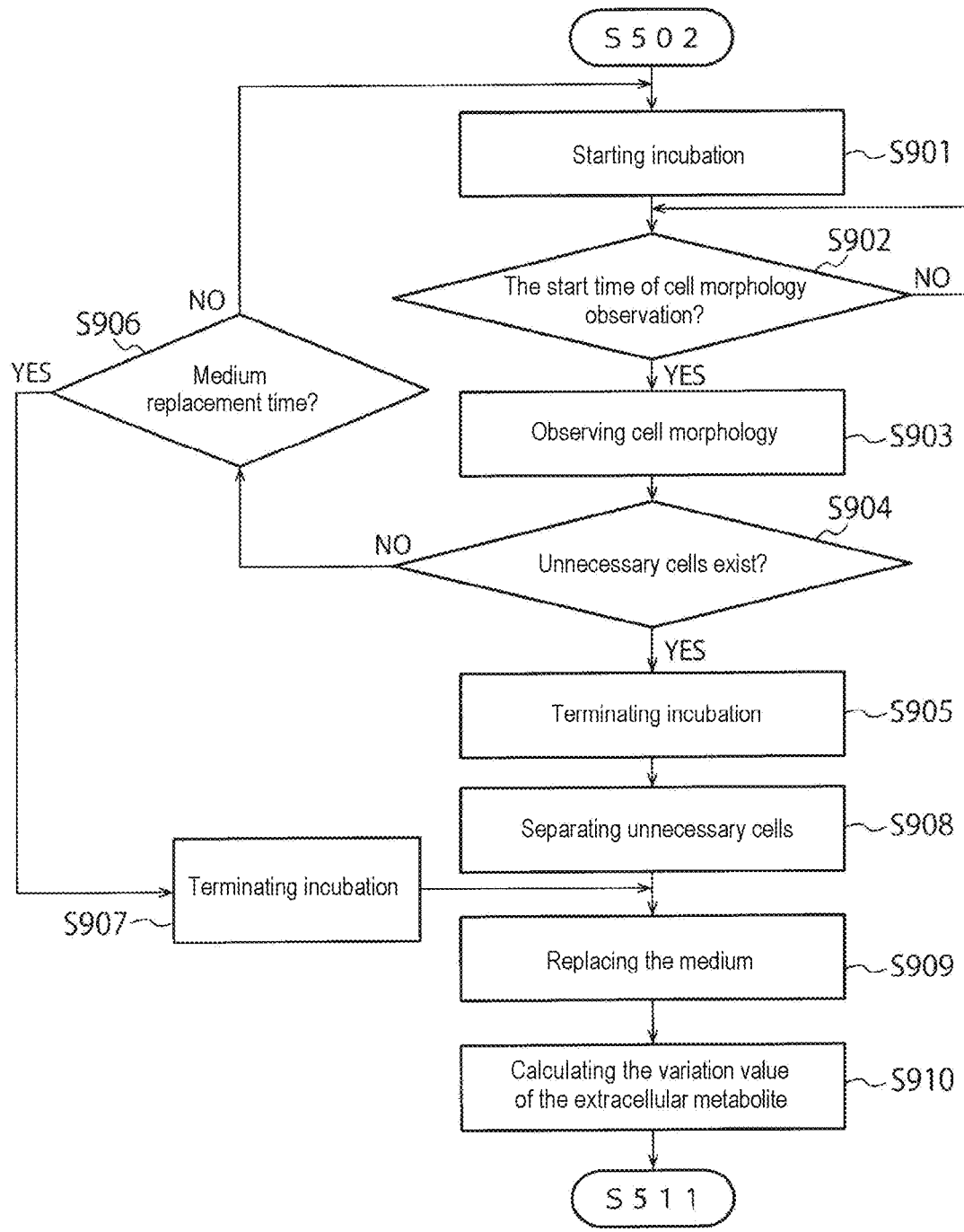
FIG. 21 is a flowchart illustrating a cell culture processing procedure (fifth embodiment) performed by the cell culture apparatus according to one embodiment of the present disclosure.

Next, a fifth embodiment of a cell culture processing procedure performed by the cell culture apparatus 100 will be described with reference to FIG. 21. FIG. 21 is a flowchart illustrating a fifth embodiment of a cell culture processing procedure performed by the cell culture apparatus 100. Respective processes of the fifth embodiment are executed in the same manner as described in the first embodiment, unless specifically mentioned otherwise.

In the fifth embodiment, the processes to step S502 and previous steps in the first embodiment are executed in the same manner as described in the first embodiment.

After step S502, the operation control part 310 controls the container transfer part 280 to transfer the culture container 10 from the cell seeding part 220 to the incubation part 230. Then, the operation control par 310 controls the incubation part 230 to start the incubation process with respect to the culture container 10 (step S901).

After step S901, the operation control part 310 determines whether the current time is the start time of the cell morphology observation process, by referring to the cell morphology observation schedule stored in the storage part 430 (step S902). Examples of the start time of the cell morphology observation process may include a time elapsed by a predetermined time period (e.g., 6, 12, 18 or 24 hours) after the start of the incubation process. For example, the start time of the cell morphology observation process is set so that the cell morphology observation process is performed multiple times at predetermined intervals (e.g., at 6-hour intervals) during a period of time from the start of the incubation process to the medium replacement process (e.g., for 24 hours after the start of the incubation process).

If it is determined at step S902 that the current time is not the start time of the cell morphology observation process (if NO at step S902), the operation control part 310 controls the incubation part 230 to continuously perform the incubation process. If it is determined at step S902 that the current time is the start time of the cell morphology observation process (if YES at step S902), the operation control part 310 controls the incubation part 230 to stop the incubation process. Subsequently, the operation control part 310 controls the container transfer part 280 to transfer the culture container 10 from the incubation part 230 to the cell morphology observation part 240. Then, the operation control part 310 controls the cell morphology observation part 240 to execute a cell morphology observation process with respect to the culture container 10 (step S903).

After step S903, the first determination part 320 determines whether a colony containing unnecessary cells (e.g., differentiation-started cells, cells of a poor growth state or the like) exists in the culture container 10, based on the observation image and/or the processed image thereof stored in the storage part 430 (step S904). In the case where the cell morphology observation process is performed twice or more during the period of time from the start of the incubation process to the end of the incubation process, the first determination part 320 determines whether a colony containing unnecessary cells exists, based on the observation images taken during the entire cell morphology observation processes and the processed images thereof. If it is determined that the colony containing unnecessary cells exists, the first determination part 320 identifies a position at which the colony containing unnecessary cells exists. The first determination part 320 stores the respective position information in the storage part 430.

If it is determined at step S904 by the first determination part 320 that the colony containing unnecessary cells exists (if YES at step S904), the operation control part 310 controls the incubation part 230 to terminate the incubation process (step S905). The operation control part 310 controls the container transfer part 280 to transfer the culture container 10 to the cell separation pan 260. Then, the operation control part 310 controls the cell separation part 260 to execute the cell separation process with respect to the culture container 10 (step S908). After step S908, the operation control pan 310 controls the container transfer part 280 to transfer the culture container 10 from the cell separation part 260 to the medium replacement part 250, and controls the medium replacement part 250 to execute the medium replacement process (step S909).

If it is determined at step S904 by the first determination part 320 that the colony containing unnecessary cells does not exist (if NO at step S904), the operation control part 310 determines whether the current time is the medium replacement time, by referring to the incubation process schedule stored in the storage part 430 (step S906). The medium replacement time may be, for example, a time elapsed by a predetermined time period (e.g., 24 hours) from the start of the incubation process.

If it is determined at step S906 that the current time is not the medium replacement time (if NO at step S906), the operation control part 310 controls the container transfer part 280 to transfer the culture container 10 from the cell morphology observation part 240 to the incubation part 230, and controls the incubation part 230 to resume the interrupted incubation process with respect to the culture container 10 (step S901).

If it is determined at step S906 that the current time is the medium replacement time (if YES at step S906), the operation control part 310 controls the incubation part 230 to terminate the incubation process (step S907). The operation control part 310 controls the container transfer part 280 to transfer the culture container 10 from the cell morphology observation part 240 to the medium replacement part 250, and controls the medium replacement part 250 to execute the medium replacement process (step S909).

After transferring the culture container 10 to the medium replacement part 250, the operation control part 310 controls the medium replacement part 250 to execute the medium replacement process with respect to the culture container 10 (step S909). The cells separated at step S908 are removed from the culture container 10 by the medium replacement process. In the case where the medium replacement process is performed after the cell separation process, the medium replacement part 250 and the cell separation part 260 serve as a cell removal pan.

After step S909, the operation control part 310 controls the first medium analysis part 291 to execute a first medium analysis process for calculating the variation value of the extracellular metabolite existing in the incubation-processed medium recovered in the medium replacement process (step S910).

After step S910, the operation control part 310 proceeds to step S511. The processes of step S515 and subsequent steps in the fifth embodiment are the same as those of the first embodiment.

In order to analyze the time-dependent change in the variation value of the extracellular metabolite, it is necessary to compare the variation value of the extracellular metabolite existing in the incubation-processed medium recovered in the current medium replacement process with the variation value of the extracellular metabolite existing in the incubation-processed medium recovered in the previous medium replacement process (specifically, in the immediately-previous medium replacement process). In order to accurately perform the comparison, it is required that the time periods of the incubation processes performed with respect to two incubation-processed media to be compared are equal to each other. In the fifth embodiment, this requirement is not met. Accordingly, at step S512 of the fifth embodiment, the operation control part 310 determines that the time-dependent change in the variation value of the extracellular metabolite is analyzable, if the variation value of the extracellular metabolite existing in the incubation-processed medium recovered in the current medium replacement process is normal, if the variation value of the extracellular metabolite existing in the incubation-processed medium recovered in the previous medium replacement process (specifically, in the immediately-previous medium replacement process) is normal and if the time periods of the incubation processes performed with respect to two incubation-processed media to be compared are equal to each other.

In the fifth embodiment, if the unnecessary cells are observed in the cell morphology observation process, it is preferred that the sum total of the time of the incubation process performed until the unnecessary cells are observed may be set as the medium replacement time in the subsequent incubation process. For example, the medium replacement time is initially set as the time elapsed by 24 hours after the start of the incubation process. However, in the case where the sum total of the time of the incubation process performed until the unnecessary cells are observed is 12 hours, the medium replacement time in the subsequent incubation process is changed to a time elapsed by 12 hours after the start of the incubation process. If the unnecessary cells are not observed in the cell morphology observation process, the medium replacement time in the current incubation process is directly used as a medium replacement time in the subsequent incubation process. If it is determined at S515 that the culture termination condition is not met (if NO at step S515), the operation control part 310 sets a new medium replacement time and then starts the incubation process.

Two or three or more of the first to fifth embodiments may be combined as long as they am combinable. For example, when the second embodiment, the third embodiment or the fifth embodiment is combined with the fourth embodiment, if it is determined in the second determination process that the cells existing in the culture container 10 are not in an undifferentiated state, the observation condition adjustment part 340 may increase the number of cell morphology observation processes performed from the start of the incubation process to the end of the incubation process. Additionally or alternatively, the observation condition adjustment part 340 may increase the observation magnification, the number of observation points or the like of the cell morphology observation process performed from the start of the incubation process to the end of the incubation process.

EXAMPLES

Hereinafter, the present disclosure will be described in detail with reference to specific examples. However, the present disclosure should not be understood a being limited by specific aspects of the examples. The present disclosure should be understood to include any modifications and changes of the disclosure disclosed in the examples.

Example 1: Study on the Relationship Between an Undifferentiated State of Pluripotent Stem Cells and Culture Medium Components In this example, a study was conducted on a medium analysis method for evaluating an undifferentiated state of pluripotent stem cells.
(Cell Culture and Recovery of Culture Medium)

In this example, human iPS cells (established by the Foundation for Biomedical Research and Innovation, Cell Evaluation Group, Kawamata Laboratory) were used as pluripotent stem cells.

Three cell groups having different differentiation states (an A group, a B group and a C group) were prepared by culturing the human iPS cells under the following three conditions. In any group, Vitronectin-N (produced by Life Technologies, Inc., product number: A14701SA) was used as ECM.

A group: iPS cells which were seeded using a culture medium (undifferentiated-state-maintaining culture medium) in which bFGF (produced by ReproCell Co., Ltd., product number: RCHEMD003) is added to a ReproFF2 medium (produced by ReproCell Co., Ltd., product number: RCHEMD006) at a final concentration of 5 ng/mL and which were then cultured using the undifferentiated-state-maintaining culture medium B group: iPS cells which were seeded using an undifferentiated-state-maintaining culture medium and which were cultured using a RepoFF2 medium (namely, a culture medium not added with bFGF that contributes to the maintenance of an undifferentiated state) from one day (day 1) after seeding the iFS cells C group: iPS cells which were seeded using an undifferentiated-state-maintaining culture medium and which were cultured using a culture medium in which retinoic acid (produced by Sigma-Aldrich, Co., Ltd., product number: R2625-50MG) as a differentiation-inducing factor is added to a ReproFF2 medium at $1 \times 10^{-8}$ mol/L, from one day (day 1) after seeding the iPS cells The cells of each of the A group, the B group and the C group were cultured using a multi-well plate (having six wells) (produced by BD Co., Ltd., product number: 353046). Five of the six wells were used in cell culture. The remaining one well was merely filled with a medium without seeding cells. The medium was entirely replaced one day (day 1), three days (day 3) and five days (day 5) after seeding the cells (2 mL per one well). The culture was performed until 7 days (day 7) after seeding the cells. The medium recovered from the five wells during the medium replacement time was used as a used medium. The medium recovered from one well was used as a control medium.
(Cell Morphology Observation)

Figure 1B:
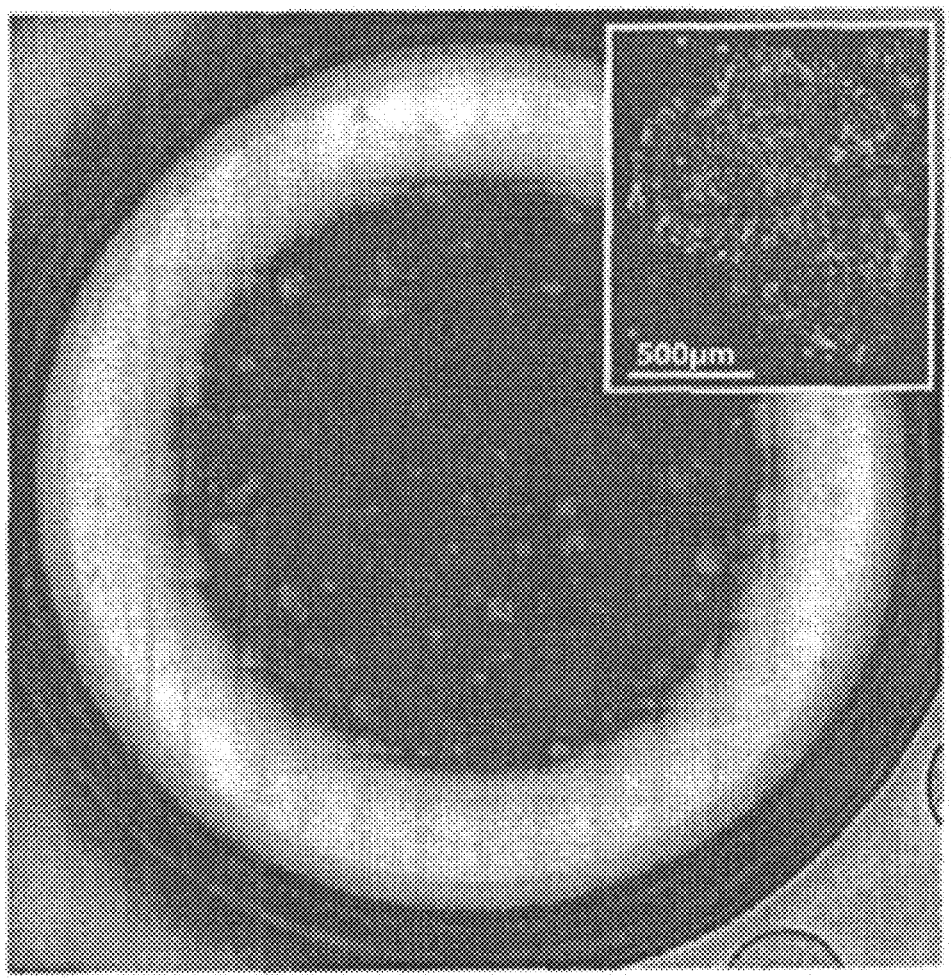
Figure 1C:
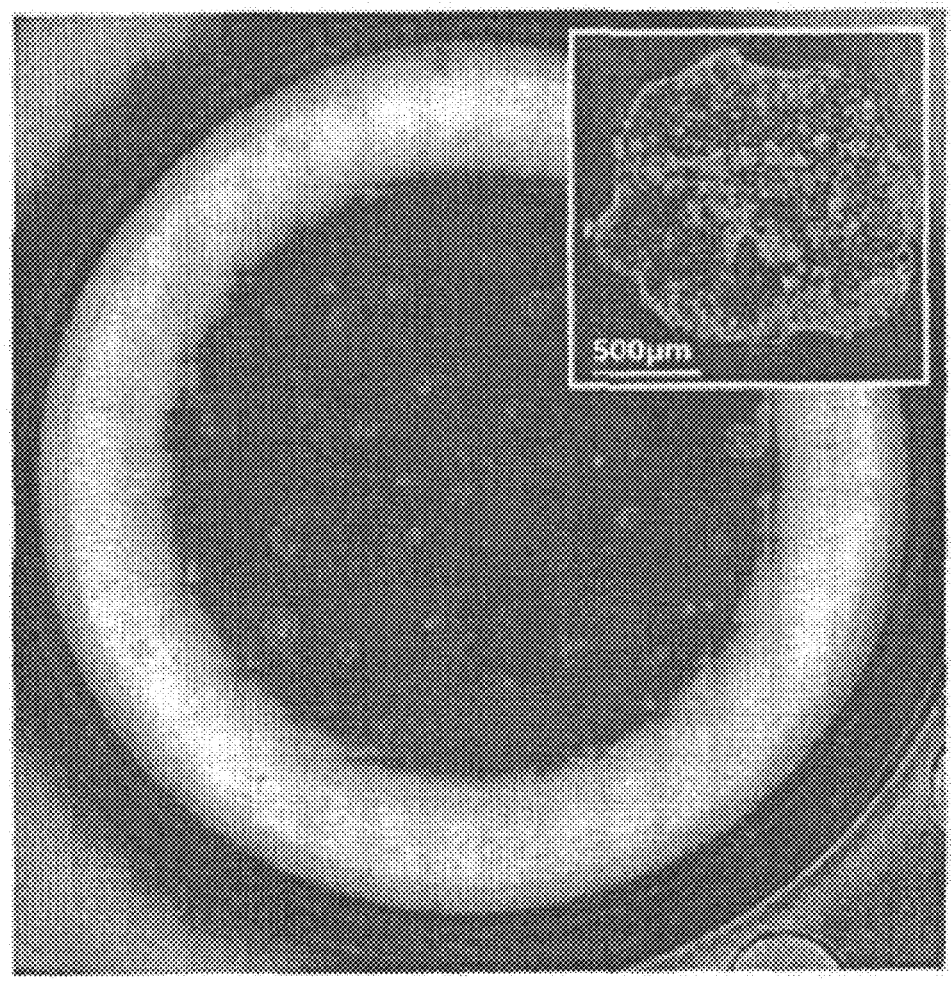

The morphology of the cells of the A group, the B group and the C group available 7 days (day 7) after seeding the cells was observed using optical microscopes with a CCD (produced by Olympus Co., Ltd., product number: IX81 and DP72). As a result, it was confirmed that the A group, the B group and the C group have characteristic cell morphologies, respectively (see FIGS. 1A to 1C). That is to say, in the A group, it was observed that the size of the cells is uniform within the colony. This is a characteristic cell morphology appearing in undifferentiated cells. Thus, it was confirmed that the A group corresponds to undifferentiated cells. On the other hand, in the B group and the C group, it was observed that the size of the cells is non-uniform within the colony. This is a characteristic cell morphology appearing in differentiated cells. Thus, it was confirmed that the B group and the C group correspond to differentiation-started cells.

(Comparison of Gene Expression)

Figure 2:
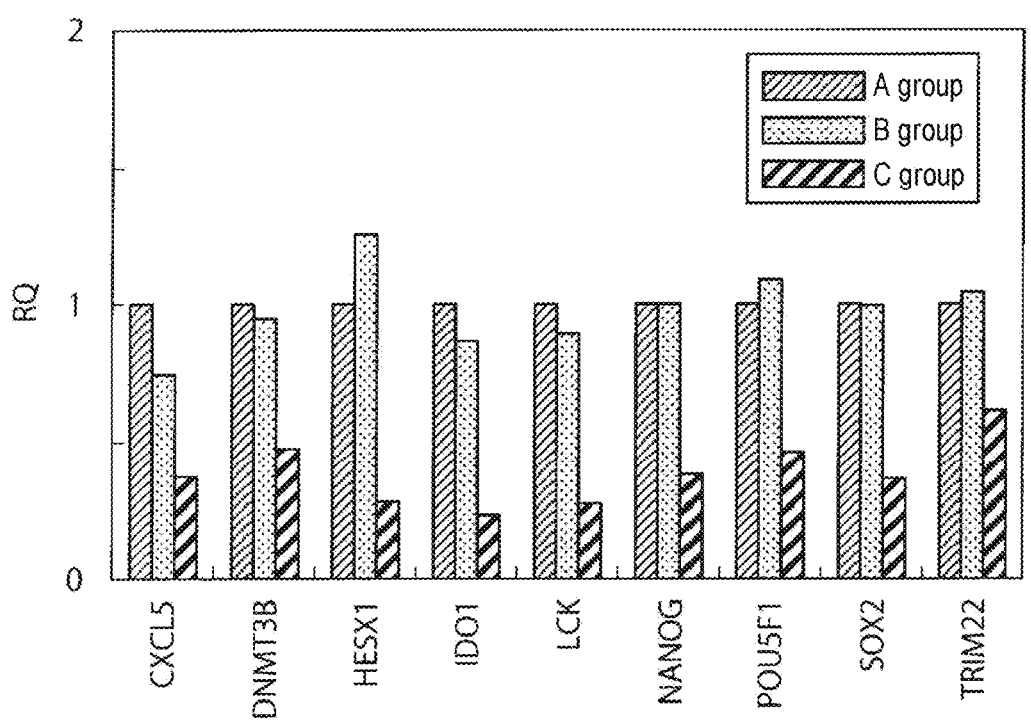
FIG. 2 is a view illustrating an expression level of an undifferentiated marker gene in (day 7) cells available 7 days after seeding cells of an A group, a B group and a C group.
Figure 3:
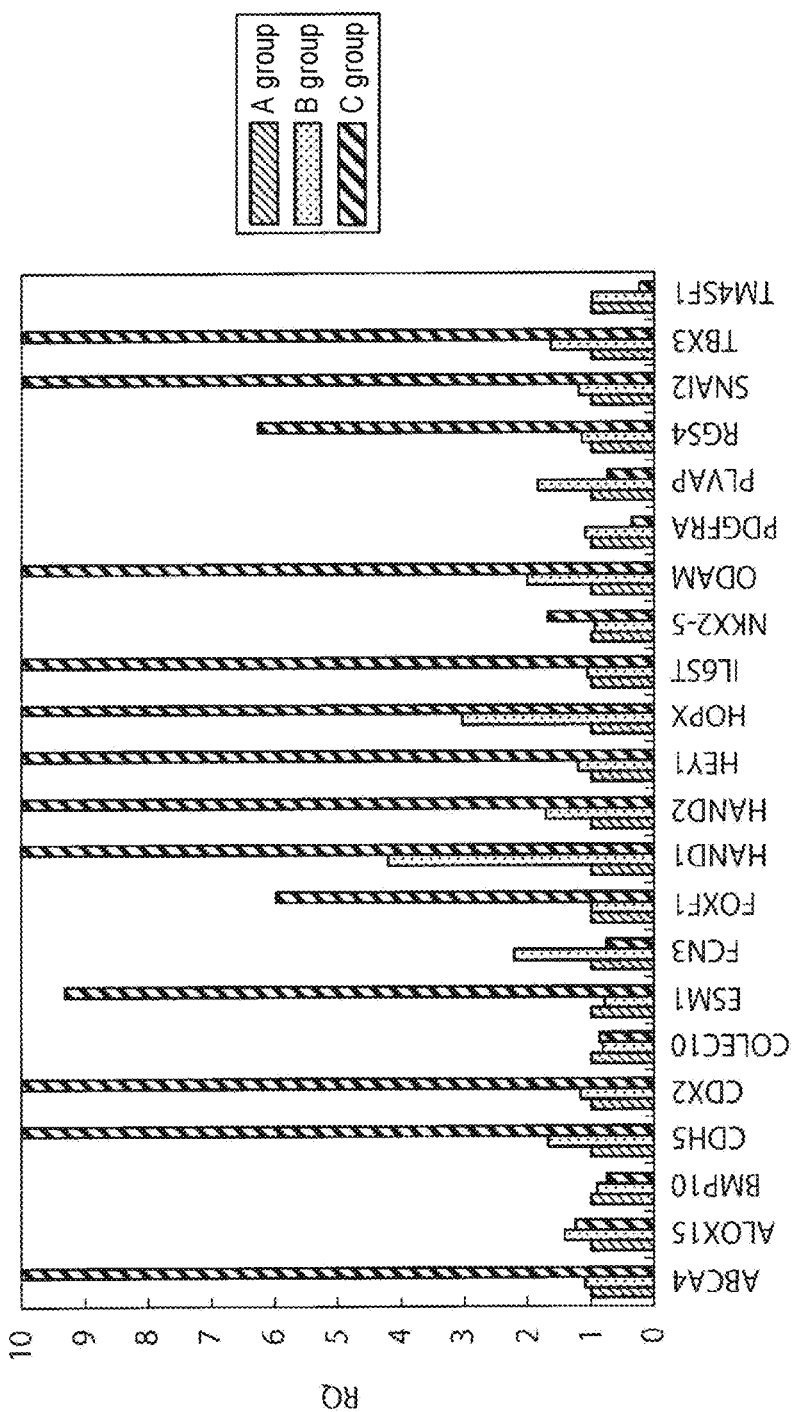
FIG. 3 is a view illustrating an expression level of a mesodermal differentiated marker gene in (day 7) cells available 7 days after seeding cells of an A group, a B group and a C group.
Figure 4A:
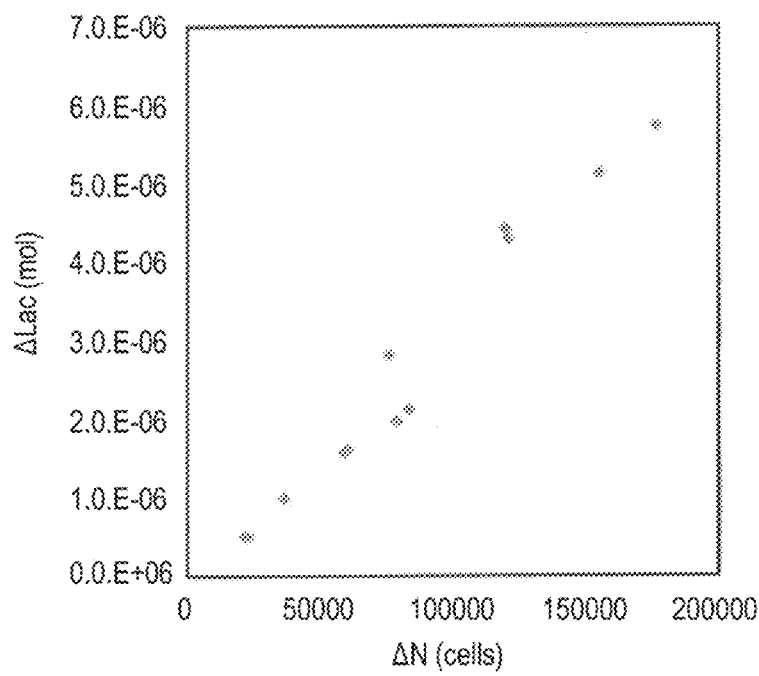
FIGS. 4A, 4B, 4C and 4D are views illustrating correlations between variation amounts $\Delta C$ (mol) ($\Delta Lac$, $\Delta Glu$, $\Delta Ala$ and $\Delta NH_3$) of the respective extracellular metabolites contained in a culture medium in which the cells of the A group are cultured and the cell number $\Delta N$ (cells) increased in respective culture periods.
Figure 4B:
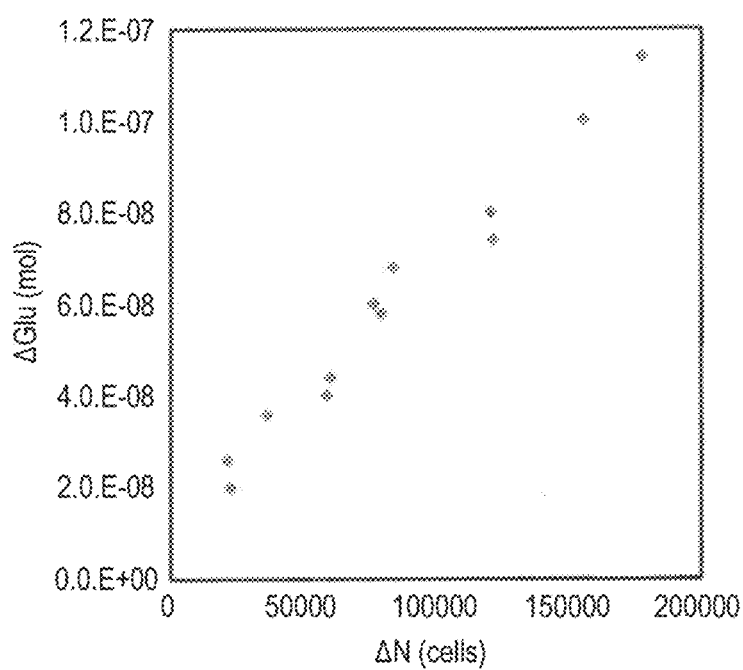
Figure 4C:
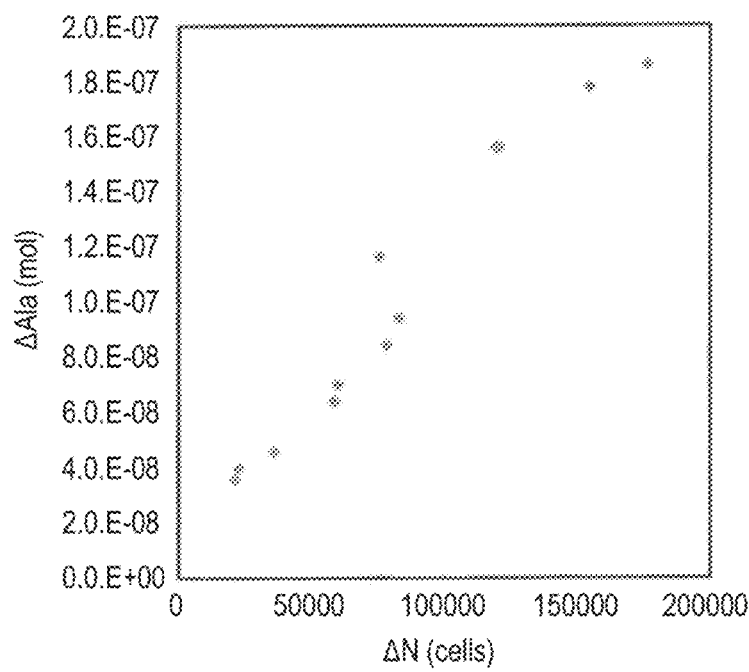
Figure 4D:
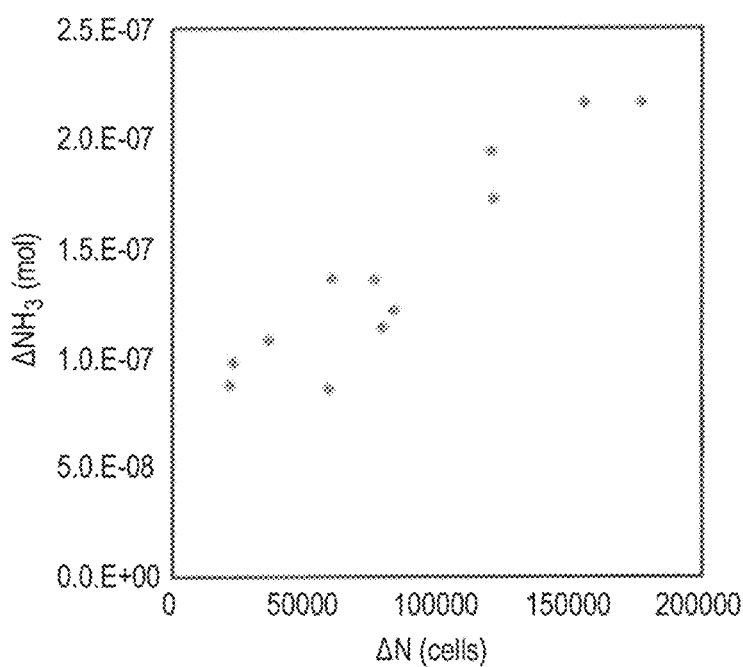

The expression levels of various kinds of genes in the cells of the A group, the B group and the C group available 7 days (day 7) after seeding the cells were analyzed using a TaqMan (trademark) hPSC Scorecard (TM) panel (produced by Life Technologies. Inc., Product Number: A15870). As a result, it was found that the expression level of various kinds of differentiated marker genes shows a small difference between the A group and the B group but shows a sharp decrease in the C group (see FIG. 2). The expression level of the various kinds of mesoderm-based differentiated markers was highest in the C group and was higher in the B group (see FIG. 3). That is to say, it was found that the B group and the C group are differentiation-started cells and the C group is cells whose differentiation is further advanced.

(Analysis of Culture Medium)

The used medium and the control medium recovered at the medium replacement time (day 1, day 3 and day 5) and at the end of culture (day 7) were used for analysis. In the analysis, the quantitative determination of the concentration C (mmol/L) of the components contained in the recovered medium, including L-lactic acid (Lac). L-glutamic acid (Glu), L-alanine (Ala) and ammonia ($NH_3$), was performed using a BioFlow (trademark) STAT biosensor BM-7M (produced by Oji Scientific Instruments Co., Ltd.). The recovered medium was frozen and stored at −80 degrees C. until the analysis. The recovered medium was thawed at a room temperature immediately prior to the analysis and was subjected to the analysis.

(Calculation of the Number of Cells)

As for the number of cells, the number of cells N (cells) was calculated by acquiring a morphology image of the cells available at the medium replacement time and at the end of culture as a digital image using phase-contrast microscopes with a CCD (produced by Olympus Co., Ltd., Product number: IX81 and DP72), finding a colony area from the acquired digital image, and setting the number of cells per unit area as 4000 cells/$mm^2$.

(Evaluation Method and Result Thereof)

The differences ($\Delta C$ (mol)=$C_{used\ medium}$−$C_{control\ medium}$) between analysis values of the used medium and the control medium were found and used as variation values (increase amount/decrease amount) of the respective extracellular metabolites during a time period from day 1 to day 3, a time period from day 3 to day 5 and a time period from day 5 to day 7 ($\Delta Lac$, $\Delta Glu$, Ala and $\Delta NH_3$).

Furthermore, the difference ($\Delta N$ (cells)) between the number of cells at the end of culture and the number of cells at each medium replacement time was found and used as the number of cells increased during a time period from day 1 to day 3, a time period from day 3 to day 5 and a time period from day 5 to day 7.

Then, the slope $\Delta C/\Delta N$ obtained by linear approximation of a plot of $\Delta N$ vs. $\Delta C$ was calculated ($\Delta Lac/\Delta N$, $\Delta Glu/\Delta N$. $\Delta Ala/\Delta N$ and $\Delta NH_3/\Delta N$).

As a result, it was confirmed that, in the A group, $\Delta Lac$, $\Delta Glu$, $\Delta Ala$ and $\Delta NH_3$ are correlated with $\Delta N$ (i.e., cell proliferation) (see FIG. 4).

Since the offset is small for $\Delta Lac/\Delta N$, a ratio of $\Delta Glu$, $\Delta Ala$ and $\Delta NH_3$ to $\Delta Lac$ was found on the basis of $\Delta Lac$ ($\Delta Glu/\Delta Lac$, $\Delta Ala/\Delta Lac$ and $\Delta NH_3/\Delta Lac$).

Figure 5:
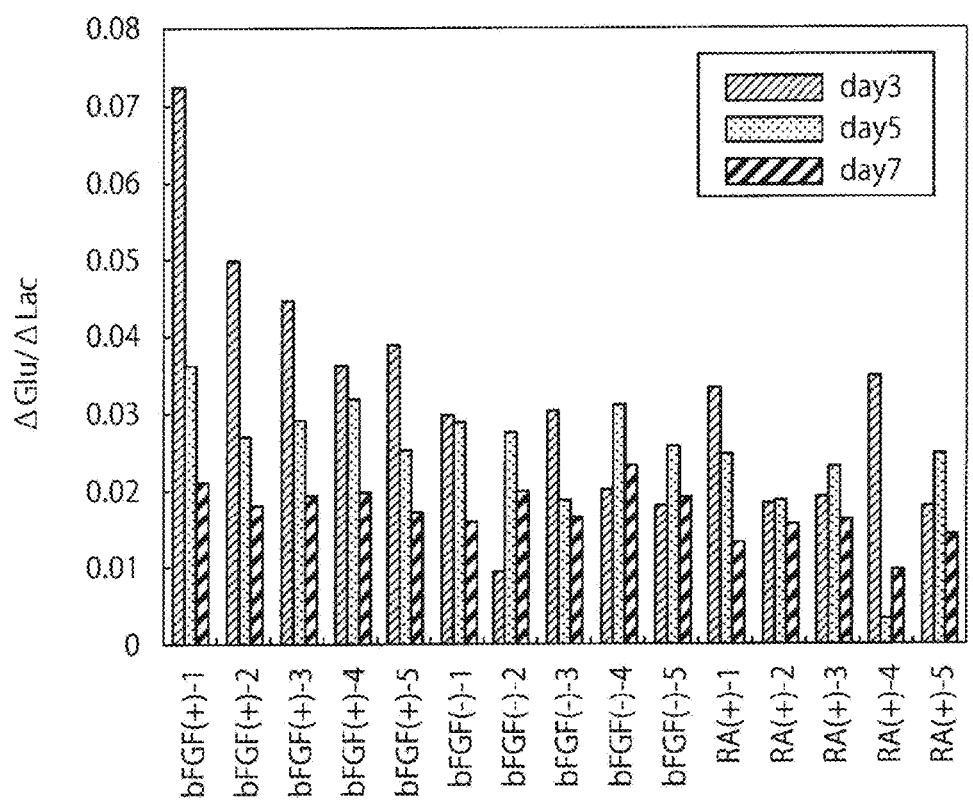
FIG. 5 is a view illustrating a change at every medium replacement time (a variation value at the medium replacement time in day 3, day 5 and day 7) in a ratio ($\Delta Glu/\Delta Lac$ of cells of an A group, a B group and a C group) of a variation value of each extracellular metabolite contained in a culture medium in which cells of an A group, a B group and a C group are cultured, namely a variation amount $\Delta C$ (mol) ($\Delta Glu$) of each extracellular metabolite, to a variation amount $\Delta Lac$ (mol) of L-lactic acid which is an extracellular metabolite contained in a culture medium in which pluripotent stem cells are similarly cultured.
Figure 6:
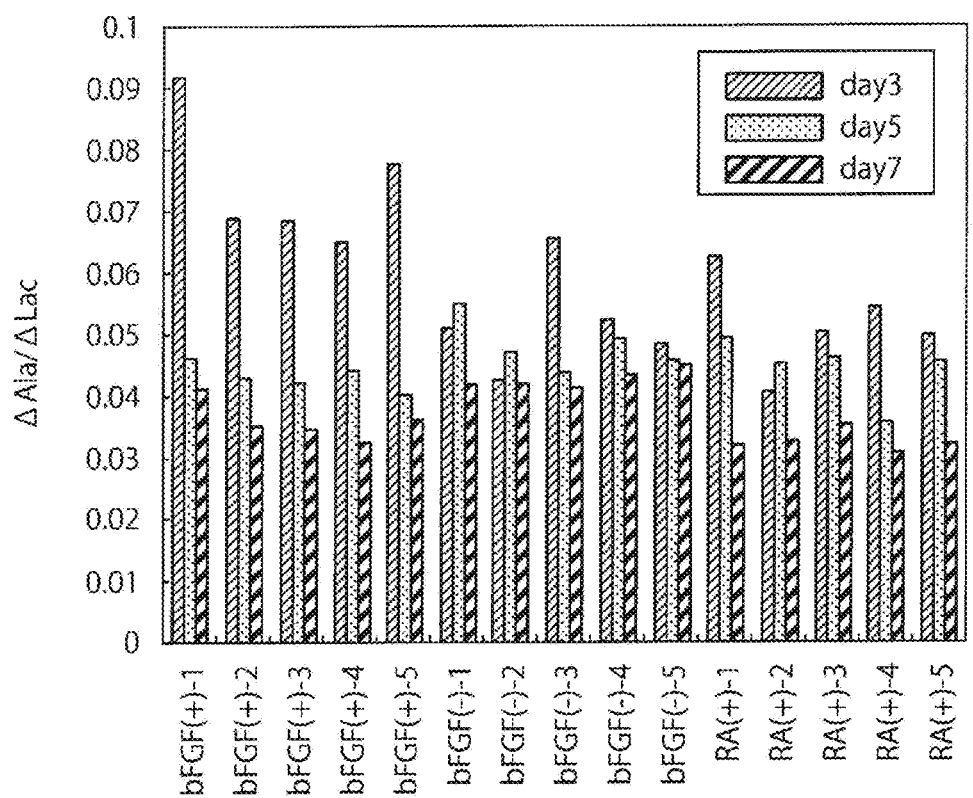
FIG. 6 is a view illustrating a change at every medium replacement time (a variation value at the medium replacement time in day 3, day 5 and day 7) in a ratio ($\Delta Ala/\Delta Lac$ of cells of an A group, a B group and a C group) of a variation value of each extracellular metabolite contained in a culture medium in which cells of an A group, a B group and a C group are cultured, namely a variation amount $\Delta C$ (mol) ($\Delta Ala$) of each extracellular metabolite, to a variation amount $\Delta Lac$ (mol) of L-lactic acid which is an extracellular metabolite contained in a culture medium in which pluripotent stem cells are similarly cultured.
Figure 7:
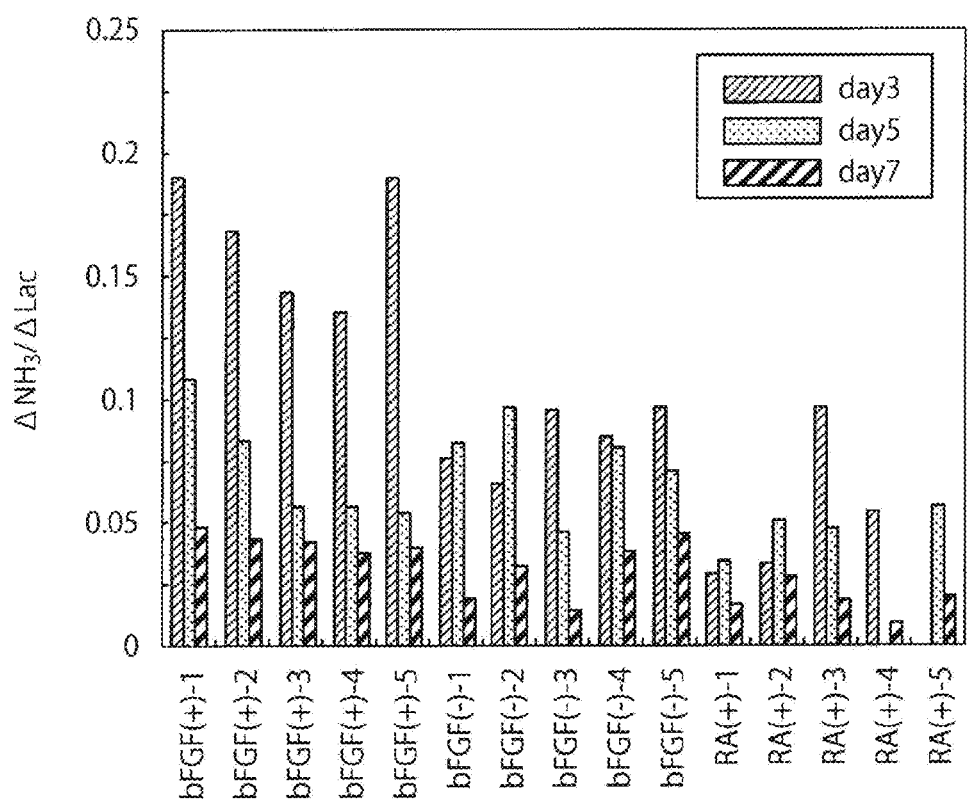
FIG. 7 is a view illustrating a change at every medium replacement time (a variation value at the medium replacement time in day 3, day 5 and day 7) in a ratio ($\Delta NH_3/\Delta Lac$ of cells of an A group, a B group and a C group) of a variation value of each extracellular metabolite contained in a culture medium in which cells of an A group, a B group and a C group are cultured, namely a variation amount $\Delta C$ (mol) ($\Delta NH_3$) of each extracellular metabolite, to a variation amount $\Delta Lac$ (mol) of L-lactic acid which is an extracellular metabolite contained in a culture medium in which pluripotent stem cells are similarly cultured.

As a result, it was confirmed that, in the A group in which the undifferentiated state is maintained, the values of $\Delta Glu/\Delta Lac$, $\Delta Ala/\Delta Lac$ and $\Delta NH_3/\Delta Lac$ are decreasing at each medium replacement time (day 3→day 5→day 7) (see FIGS. 5 to 7). On the other hand, it was confirmed that in the B group and the C group in which the differentiation is started, the values of $\Delta Glu/\Delta Lac$, $\Delta Ala/\Delta Lac$ and $\Delta NH_3/\Delta Lac$ deviate from such change in trend (see FIGS. 5 to 7). In FIGS. 5 to 7, "bFGF(+)-1" to "bFGF(+)-5" represent the group A. "bFGF(−)-1" to "bFGF(−)-5" represent the group B. "RA(+)-1" to "RA(+)-5" represent the C group. The numbers "1" to "5" added to the end of "bFGF(+)", "bFGF(−)" and "RA(+)" are the numbers (i.e., the sample numbers) for identifying the media recovered from the five wells.

From the foregoing, it was found that the undifferentiated state of the pluripotent stem cells can be determined based on the time-dependent change in $\Delta Glu/\Delta Lac$, $\Delta Ala/\Delta Lac$ and $\Delta NH_3/\Delta Lac$.

What is claimed is:

1. A method for automatically determining an undifferentiated state of pluripotent stem cells in order to subculture the pluripotent stem cells, comprising:
   automatically determining, using a computer, whether pluripotent stem cells are in an undifferentiated state or not based on a time-dependent change in a variation value of an extracellular metabolite contained in a culture medium in which the pluripotent stem cells are cultured, in order to remove or maintain the pluripotent stem cells based on determination results in the automatically determining whether the pluripotent stem cells are in the undifferentiated state or not, wherein the pluripotent stem cells are removed when the pluripotent stem cells are determined as not being in the undifferentiated state and the pluripotent stem cells are maintained when the pluripotent stem cells are determined as being in the undifferentiated state, in order to perform the automated subculture of the pluripotent stem cells,
   wherein the extracellular metabolite is at least one selected from a group consisting of L-glutamic acid, L-alanine and ammonia, and
   wherein a type of the culture medium is a culture medium configured to maintain the undifferentiated state of the pluripotent stem cells, and
   wherein the variation value is found as a ratio of a variation amount of the L-glutamic acid, the L-alanine or the ammonia to a variation amount of L-lactic acid which is a further extracellular metabolite contained in the culture medium.

2. The method of claim 1, wherein the culture medium is a culture medium used until a subsequent medium replacement is carried out from a previous medium replacement.

3. The method of claim 2, wherein a time period between culture medium replacements is 24 to 48 hours.

4. The method of claim 1, wherein the variation value is a variation value of at least one selected from a group consisting of L-glutamic acid, L-alanine and ammonia, which is available until the subsequent medium replacement after the culture medium is replaced.

5. The method of claim 1, wherein the time-dependent change in the variation value is found as an increasing or decreasing trend of a variation value obtained at each medium replacement time.

6. The method of claim 1, wherein if the variation value shows a decreasing trend as compared with a variation value in a culture medium obtained at an immediately-previous medium replacement time, it is evaluated that the pluripotent stem cells are undifferentiated cells.

7. The method of claim 6, wherein if the variation value continuously shows the decreasing trend, it is evaluated that the pluripotent stem cells are undifferentiated cells.

8. The method of claim 1, wherein if the variation value shows a trend other than the decreasing trend as compared with a variation value in a culture medium obtained at the immediately-previous medium replacement time, it is evaluated that the pluripotent stem cells are differentiation-started cells.

9. The method of claim 1, further comprising:
a step of evaluating a quality of a colony of the pluripotent stem cells based on a differential-filter-processed image of an image of a colony formed by the pluripotent stem cells.

* * * * *